United States Patent [19]

Finch et al.

[11] Patent Number: 4,853,381
[45] Date of Patent: Aug. 1, 1989

[54] ETHANOLAMINE COMPOUNDS

[75] Inventors: Harry Finch, Hitchin; Lawrence H. C. Lunts, Broxbourne; Alan Naylor, Royston; Ian F. Skidmore, Welwyn; Ian B. Campbell, Ware, all of United Kingdom

[73] Assignee: Glaxo Group Limited, London, United Kingdom

[21] Appl. No.: 919,122

[22] Filed: Oct. 15, 1986

Related U.S. Application Data

[63] Continuation-in-part of Ser. No. 724,179, Apr. 17, 1985, abandoned.

[30] Foreign Application Priority Data

Apr. 17, 1984 [GB] United Kingdom ............... 8409908
Jun. 11, 1984 [GB] United Kingdom ............... 8414858
Jun. 20, 1984 [GB] United Kingdom ............... 8415761
Jun. 20, 1984 [GB] United Kingdom ............... 8415762
Oct. 16, 1985 [GB] United Kingdom ............... 8525488
Oct. 16, 1985 [GB] United Kingdom ............... 8525489
Oct. 16, 1985 [GB] United Kingdom ............... 8525490
Oct. 16, 1985 [GB] United Kingdom ............... 8525491
Oct. 16, 1985 [GB] United Kingdom ............... 8525492

[51] Int. Cl.$^4$ ............... C07C 143/74; A61K 31/18
[52] U.S. Cl. ............... 514/211; 514/183; 514/212; 514/218; 514/228.8; 514/241; 514/247; 514/311; 514/315; 514/359; 514/365; 514/374; 514/385; 514/408; 514/522; 514/523; 514/557; 514/567; 514/595; 514/597; 514/600; 514/601; 514/629; 514/649; 514/651; 514/826; 540/544; 540/254; 546/156; 546/192; 548/122; 548/147; 548/215; 548/568; 549/366; 558/477; 562/451; 564/79; 564/80; 564/185; 564/346; 544/2; 544/5; 544/65; 544/179
[58] Field of Search ............... 564/346, 363; 514/651, 514/653; 544/2, 59, 159, 165, 179, 398, 400, 102; 546/236, 232, 233, 213; 548/567, 568, 147; 549/265, 366, 441, 443, 444

[56] References Cited

U.S. PATENT DOCUMENTS

| | | | |
|---|---|---|---|
| 2,308,232 | 1/1943 | Schening et al. | 564/357 |
| 2,900,415 | 8/1959 | Riel | 564/361 |
| 3,644,353 | 2/1972 | Lunts et al. | 544/162 |
| 3,818,101 | 6/1974 | Baile et al. | 514/653 |
| 4,026,897 | 5/1977 | Nakagawa et al. | 546/157 |
| 4,146,638 | 3/1979 | Renth et al. | 562/681 |
| 4,379,166 | 4/1983 | Neustadt et al. | 514/653 |
| 4,396,627 | 8/1983 | Ainsworth et al. | 564/363 |

FOREIGN PATENT DOCUMENTS

| | | | |
|---|---|---|---|
| 763408 | 2/1971 | Belgium | 514/653 |
| 789033 | 1/1958 | United Kingdom . | |
| 1028805 | 5/1966 | United Kingdom . | |
| 1199630 | 7/1970 | United Kingdom . | |

*Primary Examiner*—Richard L. Raymond
*Assistant Examiner*—Raymond Covington
*Attorney, Agent, or Firm*—Morgan & Finnegan

[57] ABSTRACT

The invention provides compounds of the general formula (I)

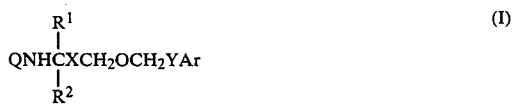

wherein
Ar represents a phenyl group optionally substituted by one or more substituents selected from halogen atoms, or the groups $C_{1-6}$alkyl, $C_{1-6}$alkoxy, nitro, $-(CH_2)_qR$ [where R is hydroxy, $-NR^3R^4$ (where $R^3$ and $R^4$ each represent a hydrogen atom or a $C_{1-4}$ alkyl group, or $-NR^3R^4$ forms a saturated heterocyclic amino group which has 5-7 ring members and optionally contains in the ring one or more atoms selected from $-O-$, or $-S-$ or a group $-NH-$ or $-N(CH_3)-$), $-NR^5COR^6$ (where $R^5$ represents a hydrogen atom or a $C_{1-4}$ alkyl group, and $R^6$ represents a hydrogen atom or a $C_{1-4}$ alkyl, $C_{1-4}$ alkoxy, phenyl or $-NR^3R^4$ group), $-NR^5SO_2R^7$ (where $R^7$ represents a $C_{1-4}$ alkyl, phenyl or $-NR^3R^4$ group), $-COR^8$ (where $R^8$ represents hydroxy, $C_{1-4}$ alkoxy or $-NR^3R^4$), $-SR^9$ (where $R^9$ is a hydrogen atom, or a $C_{1-4}$ alkyl or phenyl group), $-SOR^9$, $SO_2R^9$, or $-CN$, and q represents an integer from 0 to 3], $-(CH_2)_rR^{10}$ (where $R^{10}$ is a $C_{1-4}$ alkoxy group and r represents an integer from 1 to 3) or $-O(CH_2)_tR^{11}$ (where $R^{11}$ represents a hydroxy or $C_{1-4}$ alkoxy group and t is an integer 2 or 3), or Ar is a phenyl ring substituted by an alkylenedioxy group of formula—$O(CH_2)pO$— where p represents an integer 1 or 2;

Q represents a group of formula

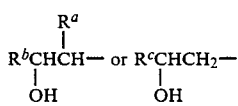

where
$R^a$ represents a hydrogen atom or a $C_{1-3}$ alkyl group,
$R^b$ represents

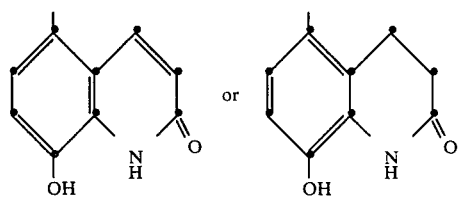

and Rc represents

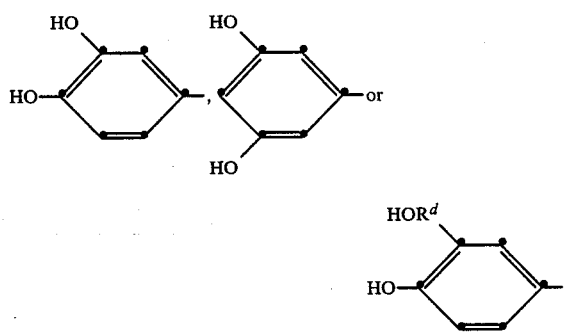

where $R^d$ represents a straight or branched $C_{2-3}$ alkylene chain;
$R^1$ and $R^2$ each represent a hydrogen atom or a $C_{1-3}$ alkyl group with the proviso that the sum total of carbon atoms in $R^1$ and $R^2$ is not more than 4;

X represents a $C_{1-7}$ alkylene, $C_{2-7}$ alkenylene or $C_{2-7}$ alkynylene chain; and Y represents a bond or a $C_1-6$ alkylene, $C_2-6$ alkenylene or $C_{2-6}$ alkynylene chain with the proviso that the sum total of carbon atoms in X and Y is 2—10, and physiologically acceptable salts and solvates (e.g. hydrates) thereof.

The compounds of formula (I) have a stimulant action at $\beta_2$-adrenoreceptors and are useful, in particular, in the treatment of diseases associated with reversible airways obstruction such as asthma and chronic bronchitis.

10 Claims, No Drawings

ETHANOLAMINE COMPOUNDS

This is a continuation-in-part application of copending U.S. application Ser. No. 724,179, filed Apr. 17, 1985 now abandoned.

This invention relates to ethanolamine compounds having a stimulant action at $\beta_2$-adrenoreceptors, to processes for their preparation, to pharmaceutical compositions containing them and to their use in medicine.

Ethanolamine derivatives of the general structures $$R^bCHCHNHR \text{ and } R^cCHCH_2NHR$$
$$\phantom{R^bCH}|\phantom{CHNHR}\phantom{aand}\phantom{R^c}|$$
$$\phantom{R^bCH}OH\phantom{CHNHR aand R^c}OH$$
with $R^a$ above the first CH in which $R^b$ and $R^c$ represent groupings of the type described hereinafter, $R^a$ represents a hydrogen atom or an alkyl group, and R represents inter alia an alkyl, aralkyl or aryloxyalkyl group have previously been described as bronchodilators having stimulant activity at $\beta$-adrenoreceptors. We have now found a novel group of ethanolamine derivatives which differ in structure from those described previously, and have a desirable and potentially useful profile of activity.

Thus, the present invention provides compounds of the general formula (I)

$$QNHCXCH_2OCH_2YAr \quad (I)$$
with $R^1$ above and $R^2$ below the C wherein

Ar represents a phenyl group optionally substituted by one or more substituents selected from halogen atoms, or the groups $C_{1-6}$alkyl, $C_{1-6}$alkoxy, nitro, $-(CH_2)_qR$ [where R is hydroxy, $-NR^3R^4$ (where $R^3$ and $R^4$ each represent a hydrogen atom or a $C_{1-4}$ alkyl group, or $-NR^3R^4$ forms a saturated heterocyclic amino group which has 5–7 ring members and optionally contains in the ring one or more atoms selected from $-O-$ or $-S-$ or a group $-NH-$ or $-N(CH_3)-$), $-NR^5COR^6$ (where $R^5$ represents a hydrogen atom or a $C_{1-4}$ alkyl group, and $R^6$ represents a hydrogen atom or a $C_{1-4}$ alkyl, $C_{1-4}$ alkoxy, phenyl or $-NR^3R^4$ group), $-NR^5SO_2R^7$ (where $R^7$ represents a $C_{1-4}$ alkyl, phenyl or $-NR^3R^4$ group), $-COR^8$ (where $R^8$ represents hydroxy, $C_{1-4}$ alkoxy or $-NR^3R^4$), $-SR^9$ (where $R^9$ is a hydrogen atom, or a $C_{1-4}$ alkyl or phenyl group), $-SOR^9$, $SO_2R^9$, or $-CN$, and q represents an integer from 0 to 3], $-(CH_2)_rR^{10}$ (where $R^{10}$ is a $C_{1-4}$ alkoxy group and r represents an integer from 1 to 3) or $-O(CH_2)_tR^{11}$ (where $R^{11}$ represents a hydroxy or $C_{1-4}$ alkoxy group and t is an integer 2 or 3), or Ar is a phenyl ring substituted by an alkylenedioxy group of formula $-O(CH_2)_pO-$ where p represents an integer 1 or 2;

Q represents a group of formula $$R^bCHCH- \text{ or } R^cCHCH_2-$$
$$\phantom{R^bCH}|\phantom{CH-aand}\phantom{R^c}|$$
$$\phantom{R^bCH}OH\phantom{CH-aand R^c}OH$$
with $R^a$ above the first CH where $R^a$ represents a hydrogen atom or a $C_{1-3}$ alkyl group, $R^b$ represents

[structures of hydroxyquinolinone groups] or and $R^c$ represents

[structures of dihydroxyphenyl groups], or

[structure of HOR$^d$ substituted phenyl]

where $R^d$ represents a straight or branched $C_{2-3}$ alkylene chain;

$R^1$ and $R^2$ each represent a hydrogen atom or a $C_{1-3}$ alkyl group with the proviso that the sum total of carbon atoms in $R^1$ and $R^2$ is not more than 4;

X represents a $C_{1-7}$ alkylene, $C_{2-7}$ alkenylene or $C_{2-7}$ alkynylene chain; and Y represents a bond or a $C_{1-6}$ alkylene, $C_{2-6}$ alkenylene or $C_{2-6}$ alkynylene chain with the proviso that the sum total of carbon atoms in X and Y is 2–10, and physiologically acceptable salts and solvates (e.g. hydrates) thereof.

It will be appreciated that the compounds of general formula (I) possess one or more asymmetric carbon atoms, for example the carbon atom of the $$-CH-$$
$$\phantom{-}|$$
$$\phantom{-}OH$$

group and, when $R^1$ and $R^2$ are different groups or $R^3$ is an alkyl group, the carbon atoms to which these are attached, and when $R^4$ is a branched alkylene chain.

The compounds according to the invention thus include all enantiomers, diastereoisomers and mixtures thereof, including racemates. Compounds in which the carbon atom in the $$-CH-$$
$$\phantom{-}|$$
$$\phantom{-}OH$$

group is in the R configuration are preferred.

In the general formula (I), the chain X may for example contain 2 to 7 carbon atoms and may be for example $-(CH_2)_2-$, $-(CH_2)_3-$, $-(CH_2)_4-$, $-(CH_2)_5-$, $-(CH_2)_6-$, $-CH_2C\equiv C-$, $-(CH_2)_2CH=CH-$, $-(CH_2)_2C\equiv C-$, $-CH=CHCH_2-$, $-CH=CH(CH_2)_2-$ or $-CH_2C\equiv CCH_2-$. The chain Y may be for example $-CH_2-$, $-(CH_2)_2-$, $-(CH_2)_3-$, —(CH$_2$)$_4$, —(CH$_2$)$_5$—, —(CH$_2$)$_6$—, —CH=CH—, —C≡C—, —CH$_2$CH=CH— or CH$_2$C≡C—. Preferably the total number of carbon atoms in the chains X and Y is 4 to 10 inclusive and may be, for example, 5, 6, 7 or 8. Compounds wherein the sum total of carbon atoms in th chains X and Y is 5, 6 or 7 are particularly preferred.

One preferred group of compounds of formula (I) is that in which X is C$_{1-7}$ alkylene, Y is C$_{1-6}$ alkylene and Q, Ar, R$^1$ and R$^2$ are as defined for formula (I). Particularly interesting compounds of this type are those in which X is —(CH$_2$)$_3$— or —(CH$_2$)$_4$—, and Y is —CH$_2$—, —(CH$_2$)$_2$— or —(CH$_2$)$_3$—.

Another preferred group of compounds of formula (I) is that in which X is —(CH$_2$)$_3$— or —(CH$_2$)$_4$—, and Y is a C$_{2-3}$ alkenylene or C$_{2-3}$ alkynylene group, particularly —CH=CH—, —CH$_2$CH=CH— or —CH$_2$C≡C—.

A further preferred group of compounds of formula (I) is that in which X is a C$_{3-4}$ alkenylene or C$_{3-4}$ alkynylene group, particularly —(CH$_2$)$_2$C≡C— or —CH$_2$C≡CCH$_2$— and Y is —(CH$_2$)$_3$—.

R$^1$ and R$^2$, for example, may each be methyl, ethyl, propyl or isopropyl groups except that if one of R$^1$ and R$^2$ is a propyl or isopropyl group, the other is a hydrogen atom or a methyl group. Thus for example R$^1$ may be a hydrogen atom or a methyl, ethyl or propyl group. R$^2$, for example, may be a hydrogen atom or a methyl group. R$^1$ and R$^2$ are each preferably a hydrogen atom or a methyl group.

A preferred group of compounds is that wherein R$^1$ and R$^2$ are both hydrogen atoms, or R$^1$ is a hydrogen atom and R$^2$ is a C$_{1-3}$ alkyl group, particularly a methyl group, or R$^1$ is a methyl group and R$^2$ is a methyl group.

When —NR$^3$R$^4$ in compounds of formula (I) represents a saturated heterocyclic amino group, this may have 5, 6 or 7 ring members and optionally contain in the ring a heteroatom selected from —O— or —S—, or a group —NH— or —N(CH$_3$)—. Examples of such —NR$^3$R$^4$ groups are pyrrolidino, piperidino, hexamethylenimino, piperazino, N-methylpiperazino, morpholino, homomorpholino or thiamorpholino.

Ar may be for example a phenyl group. Examples of the substituents which may be present on the phenyl group represented by Ar include chlorine, bromine, iodine, fluorine, methyl, ethyl, methoxy, ethoxy, —(CH$_2$)$_q$R [where R is hydroxy, amino, methylamino, ethylamino, dimethylamino, diethylamino, morpholino, piperidino, pyrrolidino, piperazino, N-methylpiperazino, NHCOR$^6$ (where R$^6$ is hydrogen, C$_{1-4}$ alkyl e.g. methyl, ethyl, isopropyl or n-butyl, C$_{1-4}$ alkoxy e.g. methoxy, ethoxy, isopropoxy or n-butoxy, phenyl, amino or N,N-dimethylamino), —N(CH$_3$)COCH$_3$, —NR$^5$SO$_2$R$^7$ (where R$^5$ represents a hydrogen atom or a methyl group, and R$^7$ represents phenyl, methyl, butyl, amino or dimethylaamino), —COOH, —COOCH$_3$, —COOCH$_2$CH$_3$, —CONH$_2$, —CON(CH$_3$)$_2$, —CON(CH$_2$CH$_3$)$_2$, —CON(CH$_2$CH$_2$CH$_3$)$_2$,

—SR$^9$ (where R$^9$ is methyl, ethyl or phenyl), —SOCH$_3$, —SO$_2$CH$_3$, or CN and q is zero, 1, 2 or 3], —NO$_2$, —CH$_2$OCH$_3$, —(CH$_2$)$_3$OCH$_3$, —O(CH$_2$)$_2$OH, —O(CH$_2$)$_3$OH, —O(CH$_2$)$_2$OCH$_3$, or —O(CH$_2$)$_2$OCH$_2$CH$_3$.

The phenyl group represented by Ar may optionally contain one, two or three substituents, which may be present at the 2-, 3-, 4-, 5- or 6-positions on the phenyl ring.

Particular examples of a trisubstituted phenyl group represented by Ar include phenyl substituted by an amino and two methyl groups (e.g. 3,5-dimethyl-4-aminophenyl), an amino group and two chlorine atoms (e.g. 3,5-dichloro-4-aminophenyl), or three methoxy groups (e.g. 3,4,5-trimethoxyphenyl). Particular examples of a disubstituted phenyl group represented by Ar include phenyl substituted by two hydroxyl groups (e.g. 3,5-dihydroxyphenyl), a hydroxyl and methoxy group (e.g. 3-methoxy-4-hydroxyphenyl), or two methyl groups (e.g. 3,4-dimethylphenyl).

In one preferred group of compounds, Ar is phenyl or phenyl substituted by a fluorine atom or by a hydroxy, amino, methylamino, dimethylamino, diethylamino, piperidino, pyrrolidino, —NHCOR$^6$ [where R$^6$ is hydrogen, C$_{1-4}$ alkyl (e.g. methyl, isopropyl or n-butyl), C$_{1-4}$ alkoxy (e.g. methoxy or n-butoxy), phenyl or amino], —N(CH$_3$)COCH$_3$, —NHSO$_2$CH$_3$, —NHSO$_2$(CH$_2$)$_3$CH$_3$, —CH$_2$OH, —CH$_2$NH$_2$, —COR$^8$ (where R$^8$ is methoxy, propoxy or diethylamino), —SR$^9$ (where R$^9$ is methyl, ethyl or phenyl), —CH$_2$OCH$_3$, —(CH$_2$)$_2$OH, —CH$_2$CONH$_2$, or —NO$_2$ group, or by two hydroxy groups, or Ar is 3-methoxy-4-hydroxyphenyl, 3,5-dimethyl-4-aminophenyl or 3,5-dichloro-4-aminophenyl.

A further preferred group of compounds are those in which Ar represents phenyl or phenyl substituted by methoxy and/or hydroxy or by a group selected from amino, a 5-7 membered heterocyclic amino group (e.g. pyrrolidino), —NHSO$_2$R$^7$ (where R$^7$ is C$_{1-4}$ alkyl e.g. methyl or butyl), —COR$^8$ (where R$^8$ is C$_{1-4}$ alkoxy e.g. methoxy, or NR$^3$R$^4$ where R$^3$ and R$^4$ are C$_{1-4}$ alkyl e.g. ethyl), or —SR$^9$ (where R$^9$ is C$_{1-4}$ alkyl e.g. methyl).

In the definition of Q in compounds of formula (I) the group R$^a$ may be for example a hydrogen atom or a methyl, ethyl, propyl or isopropyl group, particularly a hydrogen atom or a methyl or ethyl group. The chain R$^d$ may be for example —(CH$_2$)$_2$—, —(CH$_2$)$_3$— or

more particularly —(CH$_2$)$_2$—.

In one aspect, the invention provides a compound of formula (Ia):

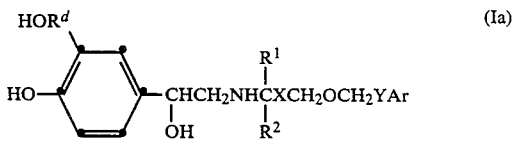

[wherein R$^1$, R$^2$ and R$^d$ are as defined for formula (I), X represents C$_{1-7}$ alkylene, Y represents a bond or C$_{2-6}$ alkylene, and Ar represents a phenyl group optionally substituted by one or two substituents selected from halogen atoms, or C$_{1-3}$alkyl or C$_{1-3}$alkoxy groups, or by an alkylenedioxy group of formula —O(CH$_2$)$_p$O— where p is 1 or 2].

In another aspect, the invention provides a compound of formula (Ia) wherein $R^1$, $R^2$, $R^d$, X, Y and Ar are as defined in formula (I), with the proviso that when X represents $C_{1-7}$ alkylene and Y represents a bond or $C_{1-6}$ alkylene, then the group Ar does not represent an unsubstituted phenyl group or a phenyl group substituted by one or two substituents selected solely from halogen atoms or $C_{1-3}$ alkyl or $C_{1-3}$ alkoxy groups or an alkylenedioxy group —$O(CH_2)_pO$—.

In another aspect, the invention provides a compound of formula (Ib)

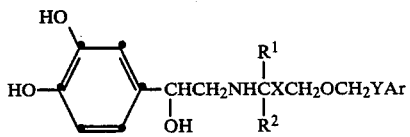

(Ib)

[wherein $R^1$ and $R^2$ are as defined for formula (I), X represents $C_{1-7}$ alkylene, Y represents a bond or $C_{2-6}$ alkylene, and Ar represents a phenyl group optionally substituted by one or two substituents selected from halogen atoms, or $C_{1-3}$alkyl or $C_{1-3}$alkoxy groups, or by an alkylenedioxy group of formula —$O(CH_2)_pO$— where p is 1 or 2].

In yet another aspect the invention provides a compound of formula (Ib) in which $R^1$, $R^2$, X, Y and Ar are as defined for formula (I) with the proviso that when X represents $C_{1-7}$ alkylene and Y represents a bond or $C_{1-6}$ alkylene, then the group Ar does not represent an unsubstituted phenyl group or a phenyl group substituted by one or two substituents selected solely from halogen atoms or $C_{1-3}$ alkyl or $C_{1-3}$ alkoxy groups or an alkylenedioxy group —$O(CH_2)_pO$—.

In a further aspect, the invention provides a compound of formula (Ic)

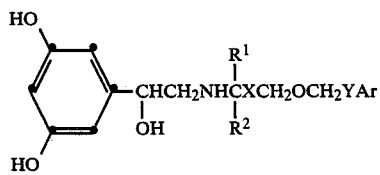

(Ic)

[wherein $R^1$ and $R^2$ are as defined for formula (I), X represents $C_{1-7}$ alkylene, Y represents a bond or $C_{2-6}$ alkylene, and Ar represents a phenyl group optionally substituted by one or two substituents selected from halogen atoms, or $C_{1-3}$alkyl or $C_{1-3}$-alkoxy groups, or by an alkylenedioxy group of formula —$O(CH_2)_pO$— where p is 1 or 2].

In yet another aspect the invention provides a compound of formula (Ic) in which $R^1$ and $R^2$ are as defined for formula (I), X represents $C_{1-7}$ alkylene, Y represents a bond or $C_{1-6}$ alkylene, and Ar is as defined in formula (IV) with the proviso that the group Ar does not represent an unsubstituted phenyl group or a phenyl group substituted by one or two substituents selected solely from halogen atoms or $C_{1-3}$ alkyl or $C_{1-3}$ alkoxy groups or an alkylenedioxy group —$O(CH_2)_pO$.

In a further aspect the invention provides a compound formula (Ic) in which $R^1$, $R^2$, X, Y and Ar are as defined in formula (I) with the provisos (i) that when X represents $C_{1-7}$ alkylene then Y represents $C_{2-6}$ alkenylene or $C_{2-6}$ alkynylene, and (ii) that when X represents $C_{1-7}$ alkylene or Y represents a bond or $C_{1-6}$ alkylene, then the group Ar does not represent an unsubstituted phenyl group or a phenyl group substituted by one or two substituents selected solely from halogen atoms or $C_{1-3}$ alkyl or $C_{1-3}$ alkoxy grups or an alkylenedioxy group —$O(CH_2)_pO$—.

In a still further aspect, the invention provides a compound of formula (Id):

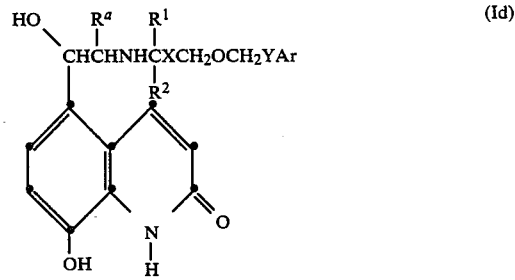

(Id)

[wherein $R^1$, $R^2$ and $R^a$ are as defined for formula (I), X represents $C_{1-7}$ alkylene, Y represents a bond or $C_{1-6}$ alkylene, and Ar represents a phenyl group optionally substituted by one or two substituents selected from halogen atoms, or $C_{1-3}$alkyl or $C_{1-3}$alkoxy groups, or by an alkylenedioxy group of formula —$O(CH_2)_pO$— where p is 1 or 2].

In yet another aspect the invention provides a compound of formula (Id) in which $R^1$, $R^2$, $R^a$, X, Y and Ar are as defined for formula (I) with the proviso that when X represents $C_{1-7}$ alkylene and Y represents a bond or $C_{1-6}$ alkylene, then the group Ar does not represent an unsubstituted phenyl group or a phenyl group substituted by one or two substituents selected solely from halogen atoms or $C_{1-3}$ alkyl or $C_{1-3}$ alkoxy groups or an alkylenedioxy group —$O(CH_2)_pO$—.

Particularly important compounds of the invention include:

2-Hydroxy-5-[1-hydroxy-2-[[6-[2-(4-methoxyphenyl)ethoxy]-hexyl]amino]ethyl]benzeneethanol;

2-Hydroxy-5-[1-hydroxy-2-[[1-methyl-6-(2-phenylethoxy)-hexyl]amino]ethyl]benzeneethanol;

5-[1-Hydroxy-2-[[1-methyl-6-(2-phenylethoxy)hexyl]amino]-ethyl]-1,3-benzenediol;

5-[1-Hydroxy-2-[[6-(4-phenylbutoxy)hexyl]amino]ethyl]-1,3-benzenediol;

5-[1-hydroxy-2-[[1-methyl-5-[3-[4-(1-pyrrolidinyl)-phenyl]propoxy]pentyl]amino]ethyl]-1,3-benzenediol;

5-[1-hydroxy-2-[[6-[3-[4-(methylthio)phenyl]propoxy]hexyl]amino]ethyl]-1,3-benzenediol;

4-[4-[[6-[[2-(3,5-dihydroxyphenyl)-2-hydroxyethyl]amino]hexyl]oxy]butyl]-N,N-diethylbenzamide;

5-[1-hydroxy-2-[[6-[2-[4-(1-pyrrolidinyl)phenyl]ethoxy]hexyl]amino]ethyl]-1,3-benzendiol; and the physiologically acceptable salts and solvates thereof.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, p-toluenesulphonates, methanesulphonates, ascorbates, salicylates, acetates, fumarates, succinates, lactates, glutarates, gluconates, tricarballylates, hydroxynaphthalenecarboxylates e.g. 1-hydroxy- or 3-hydroxy-2-naphthalenecarboxylates, or oleates. The compounds may also form salts with suitable bases. Examples of such salts are alkali metal (e.g. sodium and potassium), and alkaline earth metal (e.g. calcium or magnesium) salts.

The compounds according to the invention have a selective stimulant action at $\beta_2$-adrenoreceptors, which furthermore is of a particularly advantageous profile. The stimulant action was demonstrated in the isolated trachea of the guinea-pig, where compounds were shown to cause relaxation of PGF2α-induced contractions. Compounds according to the invention have shown an advantageous or particularly long duration of action in this test.

The selective action of compounds of the invention was demonstrated in the rat or guinea pig, where compounds were shown to have little or no effect on isolated rat or guinea pig atria ($\beta_1$-adrenoreceptor tissues) at concentrations where they cause relaxation of PGF2α-contracted isolated trachea.

The compounds according to the invention may be used in the treatment of diseases associated with reversible airways obstruction such as asthma and chronic bronchitis.

The compounds according to the invention may also be used for the treatment of premature labour, depression and congestive heart failure, and are also indicated as useful for the treatment of inflammatory and allergic skin diseases, glaucoma, and in the treatment of conditions in which there is an advantage in lowering gastric acidity, particularly in gastric and peptic ulceration.

The invention according to further provides compounds of formula (I) and their physiologically acceptable salts and solvates for use in the therapy or prophylaxis of diseases associated with reversible airways obstruction in human or animal subjects. The invention also provides compounds of formula (I) and their physiologically acceptable salts and solvates and compositions containing them in association with instructions for their use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For buccal administration the composition may take the form of tablets, drops or lozenges formulated in conventional manner.

The compounds of the invention may be formulated for parenteral administration. Formulations for injections may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.0005 mg to 100 mg (preferably 0.005 mg to 100 mg), which may be convenienty administered in one or two doses. The precise dose employed will of course depend on the age and condition of the patient and on the route of administration. Thus a suitable dose for administration by inhalation is 0.0005 mg to 10 mg (preferably 0.005 mg to 10 mg), for oral administration is 0.02 mg to 100 mg, and for parenteral administration is 0.001 mg to 2 mg (preferably 0.01 mg to 2 mg).

The compounds according to the invention may be prepared by a number of processes, as described in the following wherein Ar, Q, $R^1$, $R^2$, X and Y are as defined for general formula (I) unless otherwise specified. It will be appreciated that certain of the reactions described below are capable of affecting other groups in the starting material which are desired in the end product; this applies especially in the reduction processes described, particularly where hydrogen and a metal catalyst are used in the preparation of compounds containing an ethylene or acetylene linkage or a hydride reducing agent is used in the preparation of compounds containing an acid, ester or amide function. Care must therefore be taken in accordance with conventional practice, either to use reagents which will not affect such groups, or to perform the reaction as part of a sequence which avoids their use when such groups are present in the starting material. In the general processes described below for the preparation of both intermediate and end-products the final step in the reaction may be the removal of a protecting group.

According to one general process (1), a compound of general formula (I) may be obtained by reaction of an amine of general formula (II)

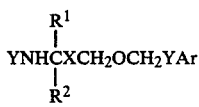  (II)

(wherein Y is a hydrogen atom or a group convertible thereto by catalytic hydrogenation) with a compound of formula

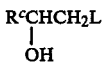

(wherein L represents a leaving group, for example a halogen atom such as chlorine, bromine or iodine, or a hydrocarbylsulphonyloxy group such as methanesulphonyloxy or p-toluenesulphonyloxy followed by removal of any protecting groups where present, as described hereinafter.

The reaction may be effected in the presence of a suitable solvent for example an alcohol, such as ethanol, a halogenated hydrocarbon e.g. chloroform, a substituted amide e.g. dimethylformamide or an ether such as tetrahydrofuran or dioxan at a temperature from ambient to the reflux, optionally in the presence of a base such as an organic amine e.g. diisopropylethylamine or an inorganic base such as sodium carbonate.

Suitable Y groups convertible into a hydrogen atom include arylmethyl groups such as benzyl, benzhydryl, or α-methylbenzyl. Such groups may be removed by hydrogenolysis in the presence of a metal catalyst (e.g. palladium on charcoal).

In another general process (2), a compound of general formula (I) may be prepared by alkylation. Conventional alkylation procedures may be used.

Thus, for example, in one process (a), a compound of general formula (I) in which $R^1$ is a hydrogen atom may be prepared by alkylation of an amine of general formula (III)

$QNR^{12}R^{13}$ (III)

(wherein $R^{12}$ is a hydrogen atom or a protecting group and $R^{13}$ is a hydrogen atom) followd by removal of any protecting group where present.

The alkylation (a) may be effected using an alkylating agent of general formula (IV):

 (IV)

(wherein L is as previously defined).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform at a temperature between ambient and the reflux temperature of the solvent.

According to another example (b) of an alkylation process, a compound of general formula (I) in which $R^1$ represents a hydrogen atom may be prepared by alkylation of an amine of general formula (III), as previously defined except that $R^{13}$ is a hydrogen atom or a group convertible thereto under the reaction conditions, with a compound of general formula (V):

$R^2COXCH_2OCH_2YAr$ (V)

in the presence of a reducing agent, followed when necessary by removal of any protecting groups.

Suitable reducing agents include hydrogen in the presence of a metal catalyst such as platinum, platinum oxide, palladium, Raney nickel or rhodium, on a support such as charcoal, using an alcohol, e.g. ethanol or an ester e.g. ethyl acetate or an ether e.g. tetrahydrofuran, or water, as reaction solvent, or a mixture of solvents, e.g. a mixture of two or more of those just described at normal or elevated temperature and pressure, for example from 20° to 100° C. and from 1 to 10 atmospheres. Alternatively when one or both of $R^5$ and $R^6$ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

Where it is desired to use a protected intermediate of general formula (III) it is particularly convenient to use hydrogen and a metal catalyst as described above with protecting groups $R^{12}$ and $R^{13}$ which are capable of being converted to a hydrogen atom under these reducing conditions. Suitable protecting groups of this type include arylmethyl groups such as benzyl, benzhydryl and α-methylbenzyl.

In a third general process (3), a compound of general formula (I) may be prepared by reduction. Thus, in one example a compound of general formula (I) may be prepared by reducing an intermediate ketone of formulae (VIa) or (VIb):

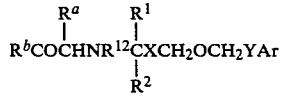 (VIa)

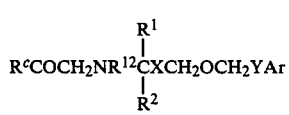 (VIb)

[wherein $R^{12}$ is as defined for general formula (III)] followed where necessary by removal of any protecting groups.

The reduction may be effected using reducing agents conventionally employed for the reduction of ketones, for example hydrogen in the presence of a metal catalyst. Alternatively the reducing agent may be for example a hydride such as diborane or a metal hydride such as lithium aluminium hydride, sodium bis(2-methoxyethoxy)-aluminium hydride, sodium borohydride or aluminium hydride. The reaction may be effected in a solvent, where appropriate an alcohol e.g. methanol or ethanol, or an ether such as tetrahydrofuran, or a halogenated hydrocarbon such as dichloromethane.

In another process, a compound of general formula (I) wherein $R^d$ is —CH(CH$_3$)— may be prepared by reaction of an aldehyde of general formula (VII):

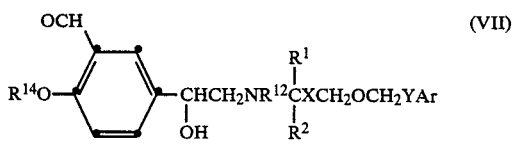

(wherein $R^{12}$ is as previously defined and $R^{14}$ is a hydrogen atom or a protecting group) with a Grignard reagent such as methyl magnesium chloride in a solvent such as tetrahydrofuan, followed when necessary by removal of any protecting groups. Suitable protecting groups $R^{14}$ are tetrahydropyranyl or aralkyl groups such as benzyl, α-methylbenzyl, diphenylmethyl or triphenylmethyl. When $R^{14}$ is a tetrahydropyranyl group this may be cleaved by hydrolysis under acidic conditions. When $R^{14}$ is an aralkyl group this may be cleaved by hydrogenolysis as previously described for the groups $R^{12}$ and $R^{13}$.

It is also possible to prepare a compound of general formula (I) by a process comprising interconversion of another compound of general formula (I).

In one example, a compound of formula (I) in which $R^b$ is the group:

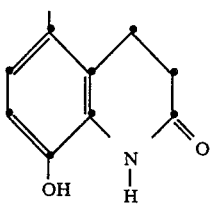

may be prepared by reduction of a corresponding compound in which $R^b$ is the group:

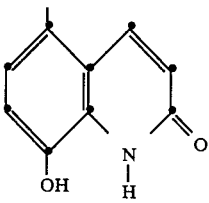

using for example hydrogen in the presence of a metal catalyst.

In the general processes described above, the compound of formula (I) obtained may be in the form of a salt, conveniently in the form of a physiologically acceptable salt. Where desired, such salts may be converted to the corresponding free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or iso-propanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods, for example by synthesis from an appropriate asymmetric starting material using any of the processes described herein, or by conversion of a mixtue of isomers of a compound of general formula (I) into appropriate diastereoisomeric derivatives e.g. salts which then can be separated by conventional means e.g. by fractional crystallisation. Alternatively, in some instances a specific diastereoisomer may be obtained through the use of particular process conditions, for example the diastereoisomers obtained from ketones of formula (VIa) where $R^a$ is an alkyl group may be determined by the method of reduction chosen. Racemates of diastereoisomers may be obtained by conventional methods of separation e.g. fractional crystallisation of a mixture of isomers of compounds of formula (I) or the salts thereof.

The intermediate compounds of formula

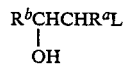

and 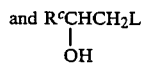

may be prepared from the corresponding haloketones $R^bCOCHR^aHal$ and $R^cCOCH_2Hal$ by reduction using for example a metal hydride such as sodium borohydride in a solvent such as ethanol. The halogen atom may be displaced to yield intermediates where L is a leaving group other than a halogen atom.

Compounds of formula

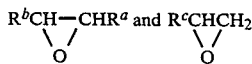

may be prepared from the corresponding compounds

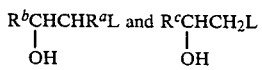

by treatment with base, for example an amine, which may be for example a compound of general formula (II), or an inorganic base such as sodium hydroxide in a solvent such as ethanol.

Intermediates of formula (III) and intermediate ketones of formulae $R^bCOCHR^aHal$ and $R^cCOCH_2Hal$ are either known compounds or may be prepared by analogous methods to those used for the preparation of the known compounds.

Intermediate ketones of formulae (VIa) and (VIb) may be prepared from ketones of formulae $R^bCOCHR$-Hal and $R^cCOCH_2Hal$ by reaction with an amine of formula (II). The reaction may be effected in a cold or hot solvent, for example tetrahydrofuran, tert-butyl methyl ether, dioxan, chloroform, dimethylformamide, acetonitrile or a ketone such as butanone or methylisobutylketone, or an ester, for example ethyl acetate optionally in the presence of a base such as diisopropylethylamine, sodium carbonate or other acid scavenger such as propylene oxide.

Intermediate aldehydes of formula (VII) may be prepared by oxidation of an alcohol of formula (VIII):

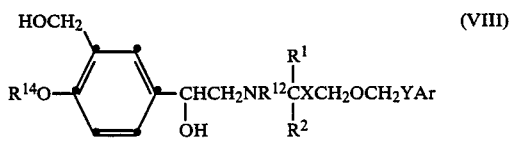

using an oxidising agent such as activated manganese dioxide in a solvent such as dichloromethane.

Intermediates of formulae (II), (IV), (V) and (VIII) may be prepared by the general methods described in U.K. Patent Specifications Nos. 2140800A and 2159151A.

The following examples illustrate the invention. Temperatures are in °C. Thin layer chromatography (T.l.c.) was carried out over $SiO_2$. "Dried" refers to drying using magnesium sulphate or sodium sulphate except where otherwise stated.

The following abbreviations are used: EA—ethyl acetate; ER—diethyl ether, DMF—dimethylformamide; THF—tetrahydrofuran; BTPC—bis(triphenylphosphine)palladium (II)chloride; TAB—tetra-n-butylammonium sulphate; DEA—diisopropylethylamine; Pd-C—palladium on charcoal; PdO-C—palladium oxide on carbon; Pt-C—platinum on charcoal; PtO—platinum oxide; [FCS] and FCC—flash column chromatography on silica (Merck 9385); [C]—column chromatography on silica (Merck 9385). Unless otherwise stated, one of the following solvent systems was used for chromatography: System A, cyclohexne-diethyl ether; System B, ethyl acetate-cyclohexane; System C, toluene-ethanol-0.88 ammonia solution; System D, hexane-diethyl ether, System E, hexane-ethyl acetate; System F, ethyl acetate-methanol-triethylamine; System G, ethyl acetate-methanol-0.88 ammonia solution; System H, toluene-ethanol-triethylamine.

The preparation of the following intermediates is described in UK Patent Specification No. 2140800A.
Intermediate 1: 7-[2-(Phenylethoxy)]-2-heptanone
Intermediate 2: N-[6-(3-Phenylpropoxy)hexyl]benzenetmethanamine hydrobromide
Intermediate 7: 4-Hydroxy-α¹-[(phenylmethyl)-6-[3-(phenylpropoxy)hexyl]amino]methyl]-1,3-benzenedimethanol
Intermediate 10: [4-[(5-Bromopentyl)oxy]butyl]benzene
Intermediate 11: 1-[2-[(6-Bromohexyl)oxy]ethyl]-4-methoxybenzene
Intermediate 17: N-[6-(4-Phenylbutoxy)hexyl]benzenemethanamine
Intermediate 21: [4-[(6-Bromohexyl)oxy]butyl]benzene
Intermediate 23: [2-[(6-Bromohexyl)oxy]ethyl]benzene
Intermediate 31: 1,1-Dimethyl-6-(2-phenylethoxy)hexamine Intermediate 3

1-[3-[2-(Acetyloxy)ethyl]-4-hydroxyphenyl]-2-bromoethanone

A solution of bromine (0.8 ml, 2.5g) in chloroform (20 ml) was added over 20 min to a stirred solution of 1-[3-[2-(acetyloxy)ethyl]-4-hydroxyphenyl]ethanone (3.26 g ) in chloroform (50 ml) containing a few drops of 45% hydrogen bromide in acetic acid. The red solution was diluted with ER (200 ml) washed with water (100 ml), 8% sodium bicarbonate (100 ml), brine (100 ml), dried and evaporated to give the title compound as an oil which solidified on standing to give a pale pink solid (4.1 g) m.p. 89°-92°. Two recrystallisations from chloroform gave a sample with m.p. 98°-99°.

Intermediate 4

2-Bromo-1-[4-hydroxy-3-(2-hydroxyethyl)phenyl]ethanone

A solution of Intermediate 3 (3.5 g) in methanol (40 ml) was diluted with 2M hyrochloric acid (10 ml) and the mixture was refluxed for 1 h. The mixture was evaporated in vacuo, to remove most of the methanol, and the residue was diluted with water (50 ml) and extracted with ER (2×50 ml). The extract was washed with 8% sodium bicarbonate (50 ml), brine (50 ml), dried and evaporated to give the title compound as an oil which solidified on standing to give a buff solid (2.05 g) m.p. 124°-125°. Recrystallisation from chloroform gave a sample with m.p. 130°-131°.

Intermediate 5

1-[4-Hydroxy-3-(2-hydroxyethyl)phenyl]-2-[(phenylmethyl [6-(3-phenyl-propoxy)hexyl]amino]ethanone A mixture of Intermediate 4 (1.0 g), Intermediate 2 (1.25 g) and N,N-diisopropylethylamine (0.8 g) in chloroform (10 ml) was stirred at 23° for 18 h. The mixture was diluted with ER (60 ml) and washed with water (2×25 ml), brine (20 ml), dried and evaporated to give an oil. Purification by [FCS] eluting with ER afforded the title compound as a viscous yellow oil (0.95 g). T.l.c. (ER) Rf 0.63.

Intermediate 6

N-[1-Methyl-6-(2-phenylethoxy)hexyl]benzenemethanamine

A solution of Intermediate 1 (11.7 g) and benzylamine (5.35 g) in toluene (50 ml) was stirred and heated under nitrogen for 2 h. The solution was hydrogenated at atmospheric pressure and room temperature over a pre-reduced 5% platinum oxide on carbon catalyst (1.5 g) in ethanol (50 ml) until the uptake of hydrogen ceased. The catalyst was removed by filtration through Hyflo and the solvent evaporated in vacuo at 50°. The crude product was purified by [FCS] elution with 5% ethanol/toluene affording the title compound as a colourless oil (10.8 g). For analytical purposes, a portion was converted to the fumarate salt by treating the amine (325 mg) with a solution of fumaric acid (116 mg) in a mixture of ER (10 ml) and methanol (2 ml). The solution was evaporated in vacuo at 40° to yield a viscous oil which when triturated with ER (10 ml) afforded the fumarate salt of the title compound as a white powder. Recrystallisation from EA gave a colourless crystalline powder (335 mg) m.p. 91°–94°.

Intermediate 8

2-Hydroxy-5-[1-hydroxy-2-[(phenylmethyl)[6-(3-phenylpropoxy)hexyl]amino]ethyl]benzaldehyde Activated manganese dioxide (ca 10 g) was added in 2 g portions to a stirred solution of Intermediate 7 (2.5 g) in dichloromethane (100 ml). Five minutes after each addition the reaction was monitored by t.l.c. (ER) and no more manganese dioxide was added when most of the starting material (Rf 0.63) had been converted into the product (Rf 0.39). The mixture was filtered through hyflo and the filtrate was evaporated to give an oil which was purified by [FCS] eluting with ER-cyclohexane (1:1) to give the title compound as a yellow oil (1.5 g). T.l.c. (ER-cyclohexane 1:1) Rf 0.63.

Intermediate 9

4-Hydroxy-α³-methyl-α¹-[[(phenylmethyl)[6-(3-phenylpropoxy)hexyl]amino]methyl]-1,3-benzenedimethanol A solution of methyl magnesium chloride in THF (2.9M, 5 ml) was added dropwise to a stirred solution of Intermediate 8 (1.1 g) in dry THF (20 ml) at 23° under nitrogen. The mixture was stirred at 23° for 0.5 h, diluted with saturated aqueous ammonium chloride (80 ml) and extracted with EA (2×50 ml). The organic phase was washed with brine (25 ml), dried and evaporated to give the title compound as a yellow oil (1.1 g). T.l.c. (ER) Rf 0.71.

Intermediate 12

N-[5-(4-(Phenylbutoxy)pentyl]benzenemethanamine

Intermediate 10 (4.0 g) was added dropwise to benzylamine (20 ml) at 110°. The solution was heated at 110°–120° for 90 min., cooled, hydrochloric acid (2M; 125 ml) was added and the mixture was extracted with EA (2×100 ml). The organic extract was washed with aqueous sodium carbonate (100 ml) and brine (100 ml), dried and evaporated. The residue was distilled to give the title compound as a colourless oil (3.3 g), b.p. 190°–195°/0.1 mmHg. T.l.c. (cyclohexane-ER 1:1) Rf 0.25

Intermediate 13

N-[6-[2-(4-Methoxyphenyl)ethoxy]hexyl]benzenemethanamine hydrochloride

Intermediate 11 (6 g) and benzylamine (10.2 g) were stirred together at 120° for 3 h. The mixture was cooled, diluted with ER (200 ml) and washed with 2N hydrochloric acid (200 ml). Both phases were filtered to afford the crude product which was dried in vacuo at 40° and recrystallised from EA-hexane to give the title compound as a white solid (5.25 g), m.p. 109°–110°.

Intermediate 14

1-[4-Hydroxy-3-(2-hydroxyethyl)phenyl]-2-[(phenylmethyl)[5-(4-phenylbutoxy)pentyl]amino]ethanone Intermediate 4 (1 g), Intermediate 12 (1.26 g) and N,N-diisopropylethyl-amine (1 g) in THF (15 ml) were stirred at reflux under nitrogen for 5 h, and left at room temperature overnight. The mixture was diluted with dichloromethane (30 ml), washed with 2N hydrochloric acid (10 ml), dried (Na₂SO₄) and evaporated in vacuo to give an oil. Purification by [FCS] (triethylamine deactivated silica) eluting with toluene-ethanol (20:1) gave a yellow oil (1.49 g). T.l.c. triethylamine deactivated silica (Toluene-ethanol 100:5) Rf 0.18

Intermediate 15

1-[4-Hydroxy-3-(2-hydroxyethyl)phenyl]-2-[6-[(4-methoxyphenyl)ethoxy]hexyl](phenylmethyl)amino]ethanone (1.09 g) T.l.c. (toluene-ethanol- 0.88 ammonia soln 39:10:1) Rf 0.45 was prepared in a similar manner to Intermediate 14 from Intermediate 4 (1 g) and Intermediate 13 (1.32 g).

Intermediate 16

1-[4-Hydroxy-3-(2-hydroxyethyl)phenyl]-2-[[1-methyl-6-(2-phenylethoxy)hexyl](phenylmethyl)amino]ethanone, (0.61 g) was prepared in a similar manner to Intermediate 14 from Intermediate 4 (1.2 g) and Intermediate 6 (1.26 g). T.l.c. (Toluene:ethanol:0.88 NH₃39:10:1) Rf 0.42.

Intermediate 18

1-(3,4-Dihydroxyphenyl)-2-[[6-(4-phenylbutoxy)hexyl](phenylmethylamino]ethanone

A solution of α-chloro-3,4-dihydroxyacetophenone (1.5 g), Intermediate 17 (3.6 g) and N,N-diisopropylethylamine (1.8 g) in THF (10 ml) was kept at 23° for 4 days. ER (70 ml) was added and the mixture was washed with 8% sodium bicarbonate (4×50 ml), brine (50 ml), dried and evaporated to give an oil. Purification by [FCS] using cyclohexane-ER (2:3) as eluant gave the title compound as a yellow oil (1.2 g). T.l.c. (ER-cyclohexane 3:2) Rf 0.28.

Intermediate 19

N-[5-(4-(Phenylbutoxy)pentyl]benzenemethanamine

Intermediate 10 (4.0 g) was added dropwise to benzylamine (20 ml) at 110°. The solution was heated at 110°–120° for 90 min and cooled. Hydrochloric acid (2M; 125 ml) was added and the mixture was extracted with EA (2×100 ml). The organic extract was washed with aqueous sodium carbonate (100 ml) and brine (100 ml), dried and evaporated. The residue was distilled to give the title compound as a colourless oil (3.3 g) b.p. 190°–195°/0.1 mmHg. T.l.c. (Cyclohexane-ER 1:1) Rf 0.25

Intermediate 20

1-[3,4-Dihydrophenyl]-2-[[5-(4-phenylbutoxy)pentyl](phenylmethyl)amino]ethanone

A solution of 2-chloro-3',4'-dihydroacetophenone (1.29 g), Intermediate 19 (2.26 g) and N,N-diisopropylethylamine (2.69 g) in dichloromethane (20 ml) was stirred under nitrogen for 20 h. Potassium iodide (1.15 g) was added, the mixture stirred for a further 6 h, diluted with dichloromethane (200 ml) and washed successively with 2N hydrochloric acid (100 ml), 8% sodium bicarbonate (100 ml) then dried (Na₂SO₄). Concentration in vacuo gave the crude product which was purified by [FCS] (triethylamine deactivated silica)

eluting with toluene-ethanol (19:1) to give the title compound as a brown oil (1.95 g).

Intermediate 22

α-[[[6-(4-Phenylbutoxy)hexyl]amino]methyl]-3,5-bis(-phenylmethoxy)benzenemethanol α-(Aminomethyl)-3,5-bis(phenylmethoxy)benzenemethanol (1.56 g), Intermediate 21 (1.16 g) and N,N-diisopropylethylamine (0.94 ml) in DMT (15 ml) were stirred at 100° under nitrogen (80 ml) for 2 h. Saturated aqueous sodium bicarbonate was added and the mixture extracted with EA (3×100 ml). The combined extracts were washed with water (80 ml), dried and evaporated to give a yellow oil. The crude oil in EA was purified by [FCS] eluting with EA-triethylamine (99:1) to give the title compound as a white solid (0.7 g), m.p. 65°–67°.

Intermediate 24

N-[6-(2-Phenylethoxy)hexyl]benzenemethanamine

Intermediate 13 (4.0 g) was added dropwise to benzylamine (20 ml) at 110°. The solution was heated at 110°–120° for 90 min., cooled, and treated with hydrochloric acid (2M; 125 ml). The mixture was extracted with EA (2×100 ml) and the extract was washed with aqueous sodium carbonate (100 ml) and brine (100 ml), dried and evaporated. Distillation of the residue gave the title compound as a colourless oil (3.2 g) b.p. 180°–190°/0.1 mmHg. T.l.c. (Cyclohexane-ER 1:1) Rf 0.2

Intermediate 25

α-[[[6-(2-Phenylethoxy)hexyl](phenylmethyl)amino]methyl]-3,5-bis(phenylmethoxy)benzenemethanol A solution of 2-[3,5-bis(phenylmethoxy)phenyl]oxirane (1.0 g) and Intermediate 24 (1.0 g) in methanol (20 ml) was refluxed for 18 h and evaporated. The residue was purified by [C] eluting with cyclohexane-ER (3:1). Repeated [C] eluting with chloroform gave the title compound as a colourless oil (0.8 g), T.l.c. (Cyclohexane-ER 3-1) Rf 0.2

Intermediate 26

2-[[5-(4-Phenylbutoxy)pentyl](phenylmethyl)amino]-1-[3,5-bis(phenylmethoxy)phenyl]ethanone A solution of 2-bromo-1-[3,5-bis(phenylmethoxy)phenyl]ethanone (2.45 g) Intermediate 19 (2.0 g) and N,N-diisopropylethylamine (0.774 g) in dichloromethane (20 ml) was stirred for 20 h at room temperature. ER (150 ml) was added and the mixture was washed with water, dried (Na₂SO₄), and evaporated. The residue was purified by [C] eluting with cyclohexane-ER (9:1) to give the title compound as a yellow oil (2.4 g). T.l.c. (Cyclohexane-ER 3:1) Rf 0.4.

Intermediate 27

1-[2-(4-Bromobutoxy)ethyl]-4-fluorobenzene

A mixture of 4-fluorobenzeneethanol (10.0 g), 1,4-dibromobutane (59.0 g), aqueous sodium hydroxide (50% w/v; 40 ml) and tetrabutylammonium bisulphate (1 g) was stirred at room temperature for 20 h, diluted with water (50 ml) and extracted with ER (2×100 ml). The dried extract was evaporated and the residue was purified by [C] eluting with cyclohexane followed by cyclohexane-ER (19:1) to give the title compound as a colourless oil (17.3 g). T.l.c. (cyclohexane-ER 9:1) Rf 0.4

Intermediate 28

7-[2-(4-Fluorophenyl)ethoxy]-2-heptanone

A mixture of Intermediate 27 (10.0 g), acetylacetone (5.0 g), potassium iodide (8.3 g), potassium carbonate (5.52 g) and ethanol (75 ml) was refluxed for 22 h, filtered, and evaporated. The residue was treated with ER (200 ml), filtered and evaporated. The resulting oil was purified by [C] eluting with cyclohexane-ER (4:1) to give the title compound as a colourless oil (4.3 g). T.l.c. (cyclohexane-ER 3:1) Rf 0.25.

Intermediate 29

1-[[2-(4-Bromobutoxy)]ethyl]-4-methoxybenzene

4-Methoxybenzeneethanol (20 g), 1,4-dibromobutane (99.31 g), tetrabutylammonium bisulphate (5.92 g) and 50% sodium hydroxide solution (200 ml) were stirred at room temperature for 18 h. The mixture was diluted with water (300 ml) and extracted with ER (2×400 ml), dried and evaporated in vacuo to give a colourless oil (39.4 g). Purification of [FCS] eluting with cyclohexane-ER (100:0→90:10) gave the title compound as a colourless oil (30.9 g). T.l.c. (cyclohexane-ER 9:1) Rf 0.36.

Intermediate 30

7-[2-(4-Methoxyphenyl)ethoxy]-2-heptanone

A mixture of Intermediate 29 (12.0 g), acetylacetone (6.0 g), potassium iodide (13.3 g), potassium carbonate (6.95 g), and ethanol (75 ml) was refluxed for 18 h, filtered, and evaporated. The residue was treated with ER (200 ml), filtered, and evaporated. The resulting oil was purified by [C] eluting with cyclohexane-ER (4:1) to give the title compound as a colourless oil (4.7 g). T.l.c. (cyclohexane-ER 3:1) Rf 0.25.

Intermediate 32

N-[1,1-Dimethyl-6-(2-phenylethoxy)hexyl]benzenemethanamine

A solution of Intermediate 31 (2.3 g), benzaldehyde (1.27 g) and 4-toluenesulphonic acid (0.02 g) in toluene (150 ml) was refluxed for 18 h and evaporated. The residue in ethanol (50 ml) was hydrogenated over 5% platinum on charcoal (0.4 g) for 2 h, filtered and evaporated. The resulting oil was purified by [C] eluting with cyclohexane-ER (3:1) to give the title compound as a colourless oil (2.1 g). T.l.c. (cyclohexane-ER 3:1) Rf 0.2

Intermediate 33

2-[[1,1-Dimethyl-6-(2-phenylethoxy)hexyl](phenylmethyl)amino-1-[3,5-bis(phenylmethoxy)phenyl]ethanone A solution of 2-bromo-1-[3,5-bis(phenylmethoxy)-phenyl]ethanone (2.5 g), Intermediate 32 (2.0 g) and N,N-diisopropylethylamine (0.77 g) in THF (25 ml) was stirred at room temperature for 2 h and refluxed for 20 h. ER (100 ml) was added and the resulting suspension was filtered, the filtrate was evaporated and the residue was purified by [C] eluting with cyclohexane-ER (4:1) to give the title compound as a pale yellow oil (1.2g). T.l.c. (cyclohexane-ER 3:1) Rf 0.4

Intermediate 34

α-[[[6-[2-(4-methoxyphenyl)ethoxy]hexyl](phenylmethyl)amino]methyl]-3,4-bis(phenylmethoxy)benzenemethanol A solution of 1 bromo-2-[3,4-bis(phenylmethoxy)phenyl]ethanone (1.0 g), Intermediate 13, free base (0.83 g) and N,N-diisopropylethylamine (0.55 g) in THF (15 ml) was stirred under nitrogen for 18 h. The solvent was evaporated in vacuo to give an oil which was dissolved in EA (50 ml) and washed with 2N hydrochloric acid (50 ml). The aqueous phase was re-extracted with EA (20 ml), the organic phases combined, dried (Na₂SO₄) and evaporated in vacuo to give a yellow oil which was purified by [FCS] (triethylamine deactivated silica) eluting with cyclohexane-EA (1:1). The resulting yellow oil was dissolved in absolute ethanol (25 ml) and THF (5 ml), the solution treated at 0° under nitrogen with sodium borohydride (0.115 g). The mixture was stirred under nitrogen for 44 h, diluted with 2N hydrochloric acid (5 ml) and the solvent evaporated in vacuo at 40°. The residue was partitioned between 2N sodium bicarbonate solution (10 ml) and EA (50 ml), the aqueous layer extracted with further EA (20 ml) and the combined organic extracts dried (Na₂SO₄) and evaporated in vacuo to give a yellow oil which was purified by [FCS] eluting with cyclohexane-EA (3:1) to give the title compound as a yellow oil (0.96 g). T.l.c. (cyclohexane-EA 3:1) Rf 0.24.

Intermediate 35

1-[3-[(6-Bromohexyl)oxy]propyl]-4-(methylthio)benzene

A mixture of 4-(methylthio)benzenepropanol (5.0 g), 1,6-dibromohexane (17.0 g), TAB (0.4 g) and aqueous sodium hydroxide (50% w/v, 20 ml) was stirred for 20 h, diluted with water (30 ml), and extracted with ether (2×100 ml). The dried extract was evaporated and the residue was purified by FCC eluting with cyclohexane followed by System A (19:1) to give the title compound as a colourless oil (7.0 g), T.l.c. (System A 9:1) Rf 0.5.

Intermediate 36

(E)-1-[4-[(6-Bromohexyl)oxy]-1-butenyl]-3-methoxy-4-(phenylmethoxy)benzene as a colourless oil (11.2 g), t.l.c. (System A 3:1) Rf 0.43 was prepared according to the method of Intermediate 35 from Intermediate 38 (12.0 g), 1,6-dibromohexane (41.2 g), 50% w/v aqueous sodium hydroxide solution (68 ml) and TAB (1.44 g), except that most of the excess dibromide was distilled off before purification by FCC eluting with System A (5:1).

Intermediate 37

N-[6-[4-(4-Nitrophenyl)butoxy]hexyl]benzenemethanamine

1-[4-[(6-Bromohexyl)oxy]butyl]-4-nitrobenzene (8.0 g) was added dropwise to benzylamine (30 ml) at 110°. The solution was heated at 110°-120° for 2 h, treated with hydrochloric acid (2M; 200 ml), and extracted with ethyl acetate (2×150 ml). The organic extract was washed with aqueous sodium carbonate (150 ml) and brine (150 ml), dried and evaporated. The residue was purified by FCC eluting with ether to give the title compound as a pale yellow oil (5.9 g). T.l.c. Ether Rf 0.15.

Intermediate 38

(E)-4-[3-Methoxy-4-(phenylmethoxy)phenyl]-3-buten-1-ol n-Butyllithium (1.55M in hexane, 194 ml) was added dropwise to a stirred suspension of (3-hydroxypropyl)triphenylphosphonium bromide (60.3 g) in dry THF (375 ml) cooled to 0° under nitrogen. The resulting blood-red solution was stirred at 0° for 15 min and then a solution of 3-methoxy-4-(phenylmethoxy)benzaldehyde (36.3 g) in dry THF (50 ml) was added dropwise over 15 min. The mixture was stirred at 0° for 30 min, allowed to warm up to room temperature, stirred for a further 2 h and then the reaction quenched by the addition of 2N hydrochloric acid (100 ml). The THF was removed in vacuo at 40°, the aqueous residue extracted with ethyl acetate (350 ml) and the organic layer washed with 2N HCl (200 ml). The aqueous phase was extracted with further ethyl acetate (150 ml), the organic layers combined, washed with 8% sodium bicarbonate solution (200 ml) and dried. Concentration afforded a product which was purified by FCC eluting with System B (1:2) yielding the title compound as a cream powder (14.5 g) m.p. 57°-61°

Intermediate 39

1-[3,5-Bis(phenylmethoxy)phenyl]-2-[6-[(4-nitrophenyl)butoxy]hexyl]ethanone

A solution of 2-bromo-[3,5-bis(phenylmethoxy)phenyl]ethanone (2.45 g), Intermediate 37 (2.3 g) and DEA (0.775 g) in methylene chloride (20 ml) was kept at room temperature for 16 h, added to ether (150 ml), filtered, and the filtrate evaporated. The residue was purified on a column of silica (170 ml) eluting with System A (3:1) to give the title compound as a pale yellow oil (3.2 g). T.l.c. (System A 1:1) Rf 0.4.

Intermediate 40

(E)-5-[1-Hydroxy-2-[[6-[[4-[[3-methoxy-4-(phenylmethoxy)phenyl]-3-butynyl]oxy]hexyl]amino]ethyl]-1,3-benzenediol Intermediate 36 (1.79 g) was added dropwise over 15 min to a stirred solution of 5-[2-amino-1-hydroxyethyl]-1,3-benzenediol (1.01 g) and DEA (1.55 g) in DMF (20 ml) at 80° under nitrogen. The mixture was stirred at 80° for a further 2 h, the solvent removed in vacuo at 60° and the residual oil partitioned between water (75 ml) and ethyl acetate (100 ml). The organic phase was dried and evaporated to yield a product which was purified by FCC eluting with System C (39:10:1) to give the title compound as a viscous colourless oil (1.13 g) T.l.c. (System C 39:10:1) Rf 0.24.

Intermediate 41

6-[3-[4-(1-Pyrrolidinyl)phenyl]propoxy]-2-hexanone (i) 3-[(4-Bromobutyl)oxy]-1-propyne A mixture of 2-propyn-1-ol (10 g), 1,4-dibromobutane (60 ml), 50% aqueous sodium hydroxide (60 ml) and TAB (2 g) was stirred vigorously overnight. Water (250 ml) was added and the mixture was extracted with ether (2×200 ml). The organic extracts were dried and concentrated to a yellow oil which was purified by FCC (hexane→System D 19:1) to give the title compound as a colourless oil (19.7 g). T.l.c. (System D 19:1) Rf 0.37.

(ii)
1-[4-3-[(4-Bromobutyl)oxy]-1-propynyl]phenyl]pyrrolidine

A mixture of 1-(4-iodophenyl)pyrrolidine (22.8 g), the product of stage (i) (16.0 g), BTPC (1.5 g) and copper (I) iodide (150 mg) in DEA (125 ml) and THF (125 ml) was stirred under nitrogen for 18 h. The dark mixture was treated with ether (250 ml), the precipitate was removed by filtration and the filtrate was concentrated to a black oil which was purified by FCC (hexane→System D 9:1) to give the title compound as a pale yellow oil (3.0 g) T.l.c. (System D 9:1) Rf 0.24.

(iii)
1-[4-[3-[(4-Bromobutyl)oxy]propyl]phenyl]pyrrolidine

The product of stage (iii) (6.7 g) was hydrogenated over pre-reduced 10% PdO-C in ether-THF (1:1, 60 ml). The catalyst was removed by filtration through hyflo and the solvent was evaporated to leave the title compound as a pale brown semi-solid (6.2 g) T.l.c. (System D 9:1) Rf 0.27.

(iv)
1-[4-[3-[4-(2-Methyl-1,3-dithian-2-yl)butoxy]propyl]phenyl]pyrrolidine n-Butyllithium (1.5M in hexane, 12 ml) was added over 5 min to a stirred solution of 2-methyl-1,3-dithiane (2.4 g) in dry THF (30 ml) at 70° under nitrogen. The yellow solution was then stirred at −30° to −20° for 2 h, cooled to −78° and treated with a solution of the product of stage (iii) (6.1 g) in THF (25 ml). The solution was stirred at room temperature overnight, the solvent was evaporated and the residue was purified by FCC (hexane→System D 9:1) to give the title compound as a pale yellow oil (3.2 g) T.l.c. (System D 9:1) Rf 0.18.

(v) 6-[3-[4-(1-Pyrrolidinyl)phenyl]propoxy]-2-hexanone

A solution of the product of stage (iv) (3.2 g) in THF (50 ml) was added to a stirred suspension of mercury (II) chloride (8.5 g) and calcium carbonate (3.2 g) in methanol-water (9:1, 50 ml) and the mixture was stirred at reflux for 1 h. The reaction was filtered through hyflo, the filtrate was concentrated in vacuo and the resulting oil was dissolved in chloroform (50 ml). The resulting precipitate was removed by filtration, the solvent was evaporated and the residue was purified by FCC (System D 19:1→4:1) to give the title compound as a crystalline mass (1.4 g) m.p. 30°–31°.

Intermediate 42
3,5-Bis(phenylmethoxy):2-[[(phenylmethyl[6-[4-(1-pyrrolidinyl)phenyl]ethoxy]hexyl]amino]methyl]benzememethanamine A solution of 1-[3,5-bis(phenylmethoxy)phenyl]-2-bromoethanone (1.29 g) in dry DMF (10 ml) was added dropwise to a solution of N-[6-[2-[4-(1-pyrrolidinyl)phenyl ethoxy]hexyl]benzeneme thanamine (1.2 g) and DEA (0.41 g) in dry DMF (12 ml) under nitrogen. The mixture was stirred at room temperature under nitrogen overnight, the solvent was evaporated and the residue was dissolved in absolute ethanol (30 ml). The solution was cooled in an ice bath and treated portionwise with sodium borohydride (1.3 g) under nitrogen. After 5 h the solution was brought to room temperature, stirred for a further 10 min then concentrated to a yellow foam. The foam was partitioned between ethyl acetate (50 ml) and water (50 ml) and the organic layer washed with brine (50 ml), dried and concentrated to a yellow oil which was purified by FCC eluting with System E to give the title compound as a yellow oil (1.35 g). T.l.c. (System E 2:1) Rf 0.4.

Intermediate 43
N-[4-[3-[[6-[(Phenylmethyl)amino]hexyl]oxy]propyl]phenyl]butanesulphonamide (i)
N-[4-[3-[(6-Bromohexyl)oxy]-1-propynyl[phenyl]-butanesulphonamide A mixture of N-(4-iodophenyl)butanesulphonamide (2.01 g), 1-bromo-6-[(2-propynyl)oxy]hexane (1,3 g), BTPC (80 mg), copper (I) iodide (10 mg) and DEA (6.5 ml) in THF (6.5 ml) was stirred under nitrogen for 18h. The mixture was diluted with ether (50 ml) and filtered. The filtrate was evaporated in vacuo to give a dark brown oil which was purified by FCC eluting with System E (4:1) to give the title compound as a colourless oil (1.17 g). T.l.c. (System E 4:1) Rf 0.1.

(ii)
N-[4-[3-[(6-Bromohexyl)oxy]propyl]phenyl]butanesulphonamide

A solution of the product of stage (i) (1.32 g) in absolute ethanol (70 ml) was hydrogenated over a pre-reduced 10% PdO-C catalyst (250 mg) in absolute ethanol (10 ml). The mixture was filtered through hyflo and evaporated in vacuo to give the title compound as a yellow oil (1.06 g). T.l.c. (System C 40:10:1) Rf 0.67.

(iii)
N-[4-[3-[[6-[(Phenylmethyl)amino]hexyl]oxy]propyl]phenyl]butanesulphonamide The product of stage (ii) (0.85 g) was added dropwise over 5 min to stirred benzylamine (1.17 g) at 120° under nitrogen. The solution was stirred at 120° under nitrogen for 2 h, cooled and diluted with dichloromethane (100 ml). The mixture was washed with 2N hydrochloric acid (40 ml), the aqueous phase was re-extracted with further dichloromethane (2×40 ml), and the combined organic extracts were washed with 8% sodium bicarbonate solution (80 ml), dried and evaporated in vacuo to give the title compound as a yellow oil (0.5 g). T.l.c. (System C 39:10:2) Rf 0.49.

Intermediate 44
N-[4-[3-[[6-[[2-[4-Hydroxy-(2-hydroxyethyl)phenyl]-2-oxoethyl](phenylmethyl)amino]hexyl]oxy]propyl]phenyl]butanesulphonamide 2-Bromo-1-[4-hydroxy-3-(2-hydroxyethyl)phenyl]ethanone (0.25 g), Intermediate 43 (0.45 g) and DEA (0.14 g) in DMF (10 ml) were stirred together at room temperature under nitrogen for 48 h. The solution was diluted with water (50 ml), extracted with ethyl acetate (3×50 ml), dried and evaporated in vacuo to give an oil. Purification by FCC eluting with System C (189:10:1) gave the title compound as a yellow oil (0.51 g) T.l.c. (System C 189:10:1) Rf 0.09.

Intermediate 45
(E)-N-[6-[[4-[3-Methoxy-4-(phenylmethoxy)phenyl]-3-butenyl]oxy]hexyl]benzenemethanamine Intermediate 36 (2.23 g) was added dropwise to benzylamine (10 ml) stirred at 120° under nitrogen and the solution heated at 120° for a further 2 h. The mixture was cooled, poured into 2N hydrochloric acid (100 ml) and extracted with dichloromethane (2×75 ml). The organic layer was washed with 2N hydrochloric acid, 8% sodium bicarbonate solution (75 ml), dried and concentrated in vacuo at 40° to afford the title compound as a pale yellow oil (2.32 g). T.l.c. (System C 39:10:1) Rf 0.41.

Intermediate 46

(E)-1-(3,4-Dihydroxyphenyl)-2-[[6-[[4-[3-methoxy-4-(phenylmethoxy)phenyl]-3-butenyl]oxy]hexyl](phenylmethyl)amino]ethanone A mixture of 2-chloro-1-(3,4-dihydroxyphenyl)ethanone (0.56 g), Intermediate 45 (1.42 g), DEA (1.16 g) and potassium iodide (0.1 g) was stirred in DMF (10 ml) under nitrogen for 20 h. The solvent was removed in vacuo at 50° and the residual oil partitioned between ethyl acetate (75 ml) and 2N hydrochloric acid (75 ml). The aqueous phase was extracted with ethyl acetate (25 ml), the combined organic layers washed successively with 8% sodium bicarbonate solution (50 ml) and pH 7 buffer solution (75 ml) and then dried. The solution was evaporated onto 'flash' silica, and the resulting impregnated material was purified by FCC eluting with System A (1:4) yielding the title compound as a viscous pale yellow oil (1.17 g) T.l.c. (System A 1:4) Rf 0.43.

Intermediate 47

N,N-Diethyl-4-[4-[[6-[(phenylmethyl)amino]hexyl]oxy]-1-butynyl]benzamide

A mixture of N,N-diethyl-4-iodobenzamide (5.79 g), BTPC (130 mg) and copper (I) iodide (80 mg) in diethylamine (100 ml) was stirred under nitrogen at room temperature for 16 h. The solvent was evaporated and the residue was partitioned between ethyl acetate (200 ml) and 8% aqueous sodium bicarbonate (200 ml). The organic layer was washed with water (50 ml) and brine (50 ml), dried and concentrated to an oil (9.7 g) which was purified by FCC eluting with ethyl acetate-triethylamine (100:1) to give the title compound as a red oil (4.60 g). T.l.c. (EtOAc+few drops Et₃N) Rf 0.15.

Intermediate 48

N,N-Diethyl-4-[4-[[6-[[2-(1,2-dihydro-8-hydroxy-2-oxoquinolin-5-yl)-2-hydroxyethyl](phenylmethyl)amino]hexyl]oxy]butyl]benzamide A solution of 5-oxiranyl-8-(phenylmethoxy)-2(1H)-quinolinone (850 mg) and Intermediate 47 (1.26 g) in methanol (20 ml) was stirred at reflux under nitrogen for 18 h. The solvent was evaporated and the residual oil was purified by FCC eluting with System E (4:1)→ethyl acetate to give a yellow oil. The oil in ethanol (20 ml) was hydrogenated over pre-reduced 10% PdO-C (100 mg). The catalyst was removed by filtration through hyflo, the ethanol was evaporated and the product was purified by FCC eluting with System C (80:20:1) to give the title compound as a pale yellow solid (130 mg) m.p. 101°-103°.

Example 1

2-Hydroxy-5-[1-hydroxy-2-[[6-(3-phenylpropoxy)hexyl]amino]ethyl]benzeneethanol

A solution of Intermediate 5 (0.5 g) in absolute ethanol (25 ml) was hydrogenated at room temperature and atmospheric pressure over 10% palladium on carbon and 10% platinum on carbon catalysts (0.15 g of each). When hydrogen absorption (49 ml) ceased the mixture was filtered and the filtrate evaporated to give an oil. Purification by [FCS] (triethylamine-deactivated silica) eluting with EA (9:1) afforded the title compound as an oil which on trituration with ER gave a white solid (0.31 g) m.p. 64°-65°. T.l.c. triethylamine-deactivated silica (EA-methanol 9:1) Rf 0.21

Example 2

4-Hydroxy-$\alpha^3$-methyl-$\alpha^1$-[[[6-(3-phenylpropoxy)hexyl]amino]methyl]-1,3-benzenedimethanol (0.52 g) was prepared in a similar manner to Example 1 from Intermediate 9 (1.1 g). T.l.c. triethylamine-deactivated silica (EA-methanol 9:1) Rf 0.4.

Example 3

2-Hydroxy-5-[1-hydroxy-2-[[5-(4-phenylbutoxy)pentyl]amino]ethyl]benzeneethanol

A solution of Intermediate 14 (1.36 g) in absolute ethanol (55 ml) was hydrogenated over a mixture of 10% palladium on charcoal (140 mg) and 5% platinum on charcoal (140 mg) catalysts. The mixture was filtered through hyflo and evaporated in vacuo to give a colourless oil (1.12 g). Trituration with ER afforded the title compound as a white solid (0.6 g) m.p. 65°-67°.

Analysis Found: C, 71.95; H, 8.68; N, 3.45. $C_{25}H_{37}NO_4$ requires C, 72.25; H, 8.97; N, 3.37%.

Example 4

2-Hydroxy-5-[1-hydroxy-2-[[6-[2-(4-methoxyphenyl)ethoxy]hexyl]amino]ethyl]benzeneethanol (0.42 g) was prepared in a similar manner to Example 3 from Intermediate 15 (0.79 g). m.p. 84°-85°. T.l.c. (toluene-ethanol-0.88 ammonia soloution 39:10:1) Rf 0.28.

Example 5

2-Hydroxy-5-[1-hydroxy-2-[[1-methyl-6-(2-phenylethoxy)hexyl]amino]ethyl]benzeneethanol hydrochloride (4:3)

A solution of Intermediate 16 (1 g) in absolute ethanol (40 ml) was hydrogenated over a mixture of pre-reduced 10% palladium on charcoal (100 mg) and 5% platinum on charcoal (100 mg) catalysts in absolute ethanol (10 ml) until the uptake of hydrogen (78 ml) ceased. The mixture was filtered through Hyflo and evaporated in vacuo to give a yellow oil (0.81 g). Purification by [FCS] (triethylamine deactivated silica) eluting with toluene-ethanol (19:1 ) gave a yellow oil (0.81 g) which was triturated with ehtereal hydrogen chloride to give the title compound as an off-white solid (0.29 g) m.p. 97°-100°. T.l.c. silica (Toluene-ethanol:0.88 NH₃ 39:10:1) Rf 0.33

Example 6

8-Hydroxy-5-[1-hydroxy-2-[[1-methyl-6-(2-phenylethoxy)hexyl]amino]ethyl]-2(1H)-quinolinone A slurry of 8-hydroxy-5-[[(phenylmethyl)amino]acetyl]-2 (1H)-quinolinone hydrochloride (382 mg) and Intermediate 1 (311 mg) in ethanol (20 ml) was added to a pre-reduced mixture of 10% palladium oxide on carbon (160 mg), 5% platinum oxide on carbon (160 mg), and anhydrous sodium acetate (158 mg) in ethanol (5 ml) and hydrogenated. The catalyst and solvent were removed and the residue was treated with aqueous saturated sodium bicarbonate (20 ml) and EA (15 ml). The precipitate was filtered off, dried in vacuo, and purified by [FCS] eluting with EA-methanol-triethylamine (73:25:2) to give a solid which was adsorbed onto silica gel (Merck 7734, 3 g) from methanol. The silica gel plug was applied to [FCS] eluting with EA-methanol-triethylamine (94:5:1→79:20:1) to give, after trituration with ER the title compound as a light yellow solid (63 mg), m.p. 134°–138°. T.l.c. (Toluene-ethanol-NH$_3$, 78:20:2) Rf 0.15.

Example 7

4-[1-Hydroxy-2-[[6-(4-phenylbutoxy)hexyl]amino]ethyl]-1,2-benzenediol

A solution of Intermediate 18 (1 g) in absolute ethanol (25 ml) was hydrogenated over 10% palladium on carbon (0.15 g) and 10% platinum on carbon (0.15 g) catalysts. The mixture was filtered and evaporated to give a solid which was slurried in ER (25 ml) and filterred to give the title catechol as a pale-mauve solid (0.28 g) m.p. 126°–7° (dec). T.l.c. triethylamine-deactivated silica (EA-methanol 1:1) Rf 0.72

Example 8

(1R)-4-[1-Hydroxy-2-[[1-methyl-6-(2-phenylethoxy)hexyl]amino]ethyl-1,2-benzenediol Intermediate 1 (1.00 g), R-4-(2-amino-1-hydroxyethyl)-1,2-benzenediol (722 mg), acetic acid (774 mg) and methanol (18 ml) were treated with sodium cyanoborohydride (188 mg) at room temperature. The mixture was stirred for 18 h, poured into aqueous saturated sodium bicarbonate (25 ml), extracted with EA (3×25 ml), and the combined, dried (Na$_2$SO$_4$) extracts were evaporated. The residue (1.83 g) was adsorbed onto silica gel (Merck 7734, 6 g) and subjected to [FCS] eluting with EA-methanol-triethylamine (90:9:1) to give a light brown solid (0.26 g) which was further purified by chromatography as above to give the title compound as a red solid (67 mg), m.p. 116°–119°.

Analysis Found: C, 69.6; H, 8.6; N, 3.65. C$_{23}$H$_{33}$NO$_4$.0.074Et$_3$N.0.15H$_2$O requires C, 70.8; H, 8.7; N, 3.8%.

Example 9

4-[1-Hydroxy-2-[[5-(4-phenylbutoxy)pentyl]amino]ethyl]-1,2-benzenediol

A solution of Intermediate 20 (1.89 g) in absolute ethanol (70 ml) was hydrogenated over a mixture of 5% platinum on charcoal (0.2 g) and 10% palladium on charcoal (0.2 g) catalysts until the uptake of hydrogen ceased. The mixture was filtered through hyflo, evaporated in vacuo and the crude product was purified by [FCS] (triethylamine deactivated silica) eluting with toluene-ethanol (9:1) to give a brown oil. Trituration with ER gave the title compound as a brown solid (0.21 g).

Analysis Found: C, 68.0; H, 8.2; N, 3.4. C$_{23}$H$_{33}$NO$_4$.H$_2$O requires C, 68.1; H, 8.7; N, 3.45%

Example 10

5-[1-Hydroxy-2-[[6-(4-phenylbutoxy)hexyl]amino]ethyl]-1,3-benzenediol

Intermediate 22 (0.53 g) in methanol (50 ml) was hydrogenated over 10% palladium oxide on carbon (0.26 g). The catalyst was removed by filtration through hyflo and the filtrate evaporated at reduced pressure. The resulting green gum was dissolved in EA (10 ml) and adsorbed onto silica gel (2 g Merck 7734). The dried silica gel plug was applied to [FCS] eluting with triethylamine in EA to give a clear gum. Co-evaporation with ER (2×10 ml) gave the title compound as a green friable solid (0.28 g) which on standing became a glass, m.p. 37°–39°. T.l.c. (EA-methanol-triethylamine, 89:10:1) Rf 0.3.

Example 11

5-[1-Hydroxy-2-[[6-(2-phenylethoxy)hexyl]amino]ethyl]-1,3-benzenediol benzoate (salt)

A solution of Intermediate 25 (0.7 g) in ethanol (10 ml) and THF (10 ml) was hydrogenated over 10% palladium on charcoal (0.1 g). The mixture was filtered and evaporated and the residue was purified by [C] eluting with EA-methanol-triethylamine (90:10:1) to give a colourless oil (0.3 g). The oil in chloroform (10 ml) was treated with benzoic acid (0.15 g) in chloroform (5 ml) and solvent was evaporated to leave a colourless gum. The gum was triturated with ER (3×15 ml) and dried under vacuum to give the title compound as a beige friable solid (0.27 g). T.l.c. (EA-methanol-NH$_3$ 90:10:1) Rf 0.15.

Analysis Found: C, 69.4; H, 7.7; N, 2.8. C$_{22}$H$_{31}$NO$_4$.C$_7$H$_6$O$_2$.0.3H$_2$O requires C, 69.5; H, 7.6; N, 2.8%.

Example 12

5-[1-Hydroxy-2-[[1-methyl-6-(2-phenylethoxy)hexyl]amino]ethyl]-1,3-benzenediol benzoate (salt)

A solution of 3,5-bis(phenylmethoxy)-α[[bis(phenylmethyl)amino]methyl]benzenemethanol (1.0 g) and Intermediate 1 (0.44 g) in ethanol (30 ml) and THF (10 ml) was hydrogenated over 10% palladium on charcoal (0.2g) and 5% platinum on charcoal (0.2 g). The mixture was filtered and evaporated and the residue was purified by [C] eluting with EA-methanol-triethylamine (90:10:1) to give a colourless oil. A solution of the oil and benzoic acid (0.15 g) in chloroform (10 ml) was evaporated and the residue was triturated with ER (2×10 ml) to give the title compound as an off-white solid (0.42 g) m.p. 77°–78°. T.l.c. (EA-methanol-NH$_3$ 9:1:0.1) Rf 0.2

The following compound was prepared in a similar manner to Example 11:

Example 13

5-[1-Hydroxy-2-[[5-(4-phenylbutoxy)pentyl]amino]ethyl]-1,3-benzenediol benzoate (salt)

(0.32 g) from Intermediate 26 (1.0 g). T.l.c. (EA-methanol-NH$_3$ 9:1:0.1) Rf 9.15 C$_{23}$H$_{33}$NO$_4$.C$_7$H$_6$O$_2$.0.5-H$_2$O requires C, 69.5; H, 7.8; N, 2.7%.

The following two compounds were prepared in a similar manner to Example 12:

Example 14

5-[2-[[6-[2-(4-Fluorophenyl)ethoxy]-1-methylhexyl]amino]-1-hydroxyethyl]-1,3-benzenediol, benzoate (salt)

(0.6 g) from 3,5-bis(phenylmethoxy)-α-[[bis(phenylmethyl)amino]methyl]benzenemethanol (2.2 g) and Intermediate 28 (1.0 g) m.p. 79°–83°. T.l.c. (EA-methanol-NH$_3$ 90:10:1) Rf 0.25.

Example 15

5-[1-Hydroxy-2-[[6-[2-(4-methoxyphenyl)ethoxyl]-1-methylhexyl]amino]ethyl]-1,3-benzenediol, benzoate (salt)

(0.75 g) from 3,5-bis(phenyl-methoxy)-α-[[bis(phenyl-methyl)amino]methyl]benzenemethanol (1.9 g) and Intermediate 30 (1.0 g) m.p. 74°–81°. T.l.c. (EA-methanol-NH₃ 90:10:1) Rf 0.2.

Example 16

5-[2-[1,1-Dimethyl-6-(2-phenylethoxy)hexyl]amino]-1-hydroxyethyl[-1,3-benzenediol, benzoate (salt)

from Intermediate 33 (1.2 g), m.p. 115°–119°. T.l.c. (EA-methanol-NH₃ 90:10:1) Rf 0.2, in a similar manner to Example 11.

Example 17

4-[1-Hydroxy-1-[[6-[2-(4-methoxyphenyl)ethoxy]hexyl]amino]ethyl]-1,2-benzenediol A solution of Intermediate 34 (0.85 g) in absolute ethanol (80 ml) was hydrogenated over a mixture of pre-reduced 5% platinum on charcoal (200 mg) and 10% palladium on charcoal (200 mg) catalysts in absolute ethanol (20 ml) until the uptake of hydrogen ceased (1.5 h). The solution was filtered through hyflo under nitrogen, the solvent evaporated in vacuo, and the residue triturated with ER to give the title compound as a greyish-blue solid (180 mg) m.p. 124°–125.5° (dec). T.l.c. (Toluene-ethanol-0.88 ammonia solution 39:10:1). Rf 0.24.

Example 18

(a)

5-[1-Hydroxy-2-[[6-[3-[4-(methylthio)phenyl]propoxy]-hexyl]amino]ethyl]-1,3-benzenediol, benzoate (salt)

Intermediate 35 (2.1 g) was added to a solution of 5-(2-amino-1-hydroxyethyl)benzene-1,3-diol (1.0 g) and DEA (1.55 g) in DMF (25 ml) at 70°. The mixture was heated at 75;1 ° for 3 h, evaporated under reduced pressure and the residue was purified by FCC eluting with System C (80:20:1) to give a colourless gum. The gum (0.7 g) in chloroform (10 ml) was treated with benzoic acid (0.3 g) and chloroform was evaporated. The residue was triturated with ether and dried to give the title compound as a beige friable solid (0.7 g). T.l.c. (System C 80:20:1) Rf 0.2.

Analysis Found: C, 66.0; H, 7.5; N, 2.5. C₂₄H₃₅NO₄S.C₇H₆0.5H₂O requires C, 65.9; H, 7.5; N, 2.5%. Similarly were prepared:

(b)

Methyl-4-[3-[[6-[[2-(3,5-dihydroxyphenyl)-2-hydroxyethyl]amino]-hexyl]oxy]propyl]benzoate, benzoate (salt)

as a beige solid (1.0 g) m.p. 72°–75°.

Analysis Found: C, 67.0; H, 7.3; N, 2.4. C₂₅H₃₅NO₆.C₇H₆O₂.0.3H₂O requires C, 67.1; H, 7.3; N, 2.4%. From 5-(2-amino-1-hydroxyethyl)benzene-1,3-diol (0.85 g), methyl 4-[3-[(6-bromohexyl)oxy]propyl]-benzoate (1.5 g) and DEA (1.3 g) after a reaction time of 2h.

(c)

4-[4-[[6-[[2-(3,5-Dihydroxyphenyl)-2-hydroxyethyl]amino]hexyl]oxy]butyl]-N,N-diethylbenzamide, benzoate (salt)

as a white friable solid (0.5 g) T.l.c. (T-ET-A, 80:20:1) Rf 0.2.

Analysis Found: C, 68.5; H, 8.0; N, 4.0. C₂₉H₄₄N₂O₅.1.25C₇H₆O₂.0.5H₂O requires C, 68.4; H, 8.1; N, 4.4%. From 5-(2-amino-1-hydroxyethyl)benzene-1,3-diol (0.54 g), 4-[4-[(6-bromohexyl)oxy]butyl]-N,N-diethylbenzamide (0.9 g) and DEA (0.78 g) after a reaction time of 90 min.

EXAMPLE 19

5-[2-[[6-[4-(4-Aminophenyl)butoxy]hexyl]amino]-1-hydroxyethyl]-1,3-benzenediol

A solution of Intermediate 39 (3.2 g) in ether (40 ml) and THF (10 ml) was hydrogenated over 10% Pd-C (0.2 g) and 5% Pt-C (0.2 g). The mixture was filtered and evaporated to leave a buff solid. Purification by FCC eluting with System F (90:10:1) gave the title compound as a cream solid (1.1 g) m.p. 157°–159°. T.l.c. (System G 90:10:1) Rf 0.15.

EXAMPLE 20

N-[4-[3-[[6-[[2-(3,5-Dihydroxyphenyl)-2-hydroxyethyl]amino]hexyl]oxy]propyl]phenyl]methanesulphonamide A solution of Example 24 (0.50 g) in absolute ethanol (10 ml) was hydrogenated over 10% Pd-C (0.2 g) in absolute ethanol (10 ml). The mixture was filtered and the filtrate evaporated to yield the title compound as an off-white foam (0.43 g) m.p. 66°–69°.

Analysis Found: C, 59.55; H, 7.70; N, 5.51. C₂₄H₃₆N₂O₆S.0.25H₂O requires C, 59.41; H, 7.58; N, 5.78%.

EXAMPLE 21

5-[1-Hydroxy-2-[[6-[4-(4-hydroxy-3-methoxyphenyl)-butoxy]hexyl]amino]ethyl]-1,3-benzenediol, benzoate (salt)

A solution of Intermediate 40 (1.0 g) in absolute ethanol (50 ml) was hydrogenated over 10% PdO-C (0.25 g) in absolute ethanol (15 ml). The mixture was filtered, benzoic acid (0.25 g) added to the filtrate and the solvent evaporated to yield a viscous oil. Trituration with dry ether followed by evaporation gave the title compound as an off-white foam (0.84 g) T.l.c. (System C 39:19:1) Rf 0.20.

Analysis Found: C, 66.55; H, 7.41; N, 2.36. C₂₅H₃₇NO₆.1.3C₇H₆O₂.0.5H₂O requires C, 66.41; H, 7.66; N, 2.42%.

EXAMPLE 22

5-[1-Hydroxy-2-[[1-methyl-5-[3-[4-(1-pyrrolidinyl)-phenyl]propoxy]pentyl]amino]ethyl]-1,3-benzenediol A mixture of α-(aminoethyl)-3,5-bis(phenylmethoxy) benzenemethanol (0.43 g) and Intermediate 41 (0.38 g) was stirred and refluxed in toluene (25 ml) in a Dean-Stark apparatus for 30 min when water ceased to separate. The solution was cooled, diluted with absolute ethanol (20 ml) and hydrogenated over a pre-reduced 10% PdO-C and 5% PtO-C (0.15 g) catalyst mixture in absolute ethanol (10 ml). The catalyst was removed by filtration through 'hyflo', the solvent was evaporated in vacuo at 40° and the residual product purified by FCC eluting with System C (39:10:1) yielding the title compound as a cream foam (0.26 g) m.p. 57°-60°.

Analysis Found: C, 71.20; H, 8.84; N, 6.07. $C_{27}H_{40}N_2O_4$ requires C, 71.02; H, 8.83; N, 6.13%.

EXAMPLE 23

5-[1-Hydroxy-2-[[6-[2-[4-(1-pyrrolidinyl)phenyl]ethoxy]hexyl]amino]ethyl]-1,3-benzenediol, (E) butenedioate (1:1) (salt)

Intermediate 42 (1.3 g) was hydrogenated over pre-reduced 10% Pd-C (50% aqueous paste, 400 mg) in ethanol (20 ml) and THF (5 ml). The catalyst was removed by filtration through hyflo, the ethanol was evaporated and the residue was partitioned between 8% sodium bicarbonate (25 ml) and ethyl acetate (25 ml). The aqueous layer was re-extracted with ethyl acetate (25 ml), and the combined organic extracts were washed with sodium bicarbonate (25 ml) and brine (25 ml), dried and concentrated to a yellow oil which was purified by FCC eluting with System H (98:2:1) to give a pale yellow oil (450 mg). A solution of the oil (420 mg) and fumaric acid (120 mg) in methanol (10 ml) was concentrated to a foam which was triturated several times with ether to give the title compound as a beige solid (450 mg) m.p. 49°-52°.

Analysis Found: C, 61.39; H, 7.32; N, 4.43. $C_{26}H_{38}N_2O_4.1.25C_4H_4O_4.H_2O$ requires C, 61.47; H, 7.49; N, 4.62%.

EXAMPLE 24

(Z)-N-[4-[3-[[6-[[2-(3,5-Dihydroxyphenyl)-2-hydroxyethyl]amino]hexyl]oxy]-1-propenyl]phenyl]methanesulphonamide (Z)-N-[4-[3-[(6-Bromohexyl)oxy]-1-propenyl]phenyl]methanesulphonamide (1.56 g) was added portionwise over 10 min to a stirred solution of 5-(2-amino-1-hydroxyethyl)-1,3-benzenediol (1.01 g) and DEA (1.55 g) in dry DMF (20 ml) heated to 80° under nitrogen. When the addition was complete, the mixture was stirred at 80° for 2 h, cooled and evaporated onto 'flash' silica. The impregnated material was purified by FCC eluting with System C (39:10:1) to give the title compound as a pale brown powder which was dried in vacuo at 50° for 6 h (0.75 g) m.p. 79°-82°.

Analysis Found: C, 61.56; H, 7.53; N, 5.67. $C_{24}H_{34}N_2O_6S.0.2C_7H_8$ requires C, 61.36; H, 7.22; N, 5.64%.

EXAMPLE 25

5-[1-Hydroxy-2-[[6-(4-phenylbutoxy)-4-hexynyl]amino]ethyl]-1,3-benzenediol, benzoate (salt)

A solution of 5-(2-amino-1-hydroxyethyl)-1,3-benzenediol (0.5 g), [[4-(6-iodo-2-hexynyl)oxy]butyl]benzene (1.0 g), DEA (0.7 g) and DMF (15 ml) was heated at 70°-75° for 2 h, poured into aqueous sodium bicarbonate (1M; 100 ml) and extracted with ethyl acetate (3×50 ml). The dried extract was evaporated and the residue was purified on a column of silica (90 ml) eluted with System F (90:10:1) to give an orange oil (0.11 g). The oil in chloroform (10 ml) was treated with benzoic acid (0.05 g) and the chloroform was evaporated. The residue was triturated with ether and dried to give the title compound as an orange foam (0.11 g). T.l.c. (System G 90:10:1) Rf 0.15.

Analysis Found: C, 66.5; H, 6.9; N, 2.6 $C_{24}H_{31}NO_4.C_7H_6O_2.2H_2O$ requires C, 67.0; H, 7.4; N, 2.5%

EXAMPLE 26

N-[4-[3-[[6-[[2-Hydroxy-2-[4-hydroxy-3-[(2-hydroxyethyl)]phenyl]ethyl]amino]hexyl]oxy]propyl]phenyl]butanesulphonamide, benzoate (salt)

A solution of Intermediate 44 (0.50 g) in absolute ethanol (25 ml) was hydrogenated over a mixture of pre-reduced 10% Pd-C (120 mg) and 5% Pt-C (120 mg) catalysts in absolute ethanol (5 ml). The mixture was filtered through hyflo and evaporated in vacuo to give an oil. Purification by FCC eluting with System C (64:10:1) gave a colourless oil which was dissolved in chloroform-methanol and treated with benzoic acid (0.06 g). The solution was evaporated in vacuo and triturated with diethyl ether to give the title compound as a cream foam (0.18 g). T.l.c. (System C 39:10:1) Rf 0.15.

Analysis Found: C, 63.15; H, 8.15; N, 4.1. $C_{29}H_{46}N_2O_6.C_7H_6O_2.0.5H_2O$ requires C, 63.4; H, 7.8; N, 4.1%.

EXAMPLE 27

4-[1-Hydroxy-2-[[6-[4-(4-hydroxy-3-methoxyphenyl)-butoxy]hexyl]amino]ethyl]-1,2-benzenediol, acetate (salt)

A solution of Intermediate 46 (1.1 g) in absolute ethanol (25 ml) containing glacial acetic acid (0.2 ml) was hydrogenated over a pre-reduced 10% PdO-C (0.2 g, dry) and 5% PtO (0.2 g) catalyst mixture. The catalyst was removed by filtration through 'hyflo', the solvent evaporated in vacuo at 40° and the residual dark oil triturated with dry ether to afford the title compound as a dark-grey hygroscopic glass (0.45 g), t.l.c. (System C 39:10:1) Rf 0.13.

Analysis Found: C, 62.51; H, 8.21; N, 2.61; $C_{25}H_{37}NO_6.C_2H_4O_2.0.5H_2O$ requires C, 62.77; H, 8.20; N, 2.71%

EXAMPLE 28

N,N-Diethyl-4-[4-[[6-[[2-(1,2-dihydro-8-hydroxy-2-oxoquinolin-5-yl)-2-hydroxyethyl]amino]hexyl]oxy]-butyl]benzamide, hydrochloride Intermediate 48 (120 mg) in chloroform (2 ml) was concentrated in vacuo to a gum which was hydrogenated in ethanol (10 ml) over pre-reduced 10% Pd-C (25 mg). The catalyst was removed by filtration through hyflo and the ethanol was evaporated under vacuum to leave a solid which was triturated with dry ether to give the title compound as an off-white powder (105 mg) m.p. 60°-80° (hygroscopic). T.l.c. (System C 80:20:1) Rf 0.07.

Analysis Found: C, 62.81; H, 8.01; N, 6.62; Cl, 7.27. $C_{32}H_{45}N_3O_5.1.25HCl.H_2O$ requires C, 62.46; H, 7.90; N, 6.83; Cl, 7.20%.

EXAMPLE 29

5-[1-Hydroxy-2-[[6-[3-[4-(methylthio)phenyl]propoxy]-hexyl]amino]ethyl]-1,3-benzenediol, 3-hydroxy-2-naphthalenecarboxylate (1:1) (salt)

A solution of 5-[1-hydroxy-2-[[6-[3-[4-(methylthio)-phenyl]propoxy]-hexyl]amino]ethyl]-1,3-benzenediol (422 mg) and 3-hydroxy-2-naphthalenecarboxylic acid (190 mg) in methanol (5 ml) was concentrated in vacuo and the residual oil was triturated with ether and hexane to give the title salt as a dark foam (470 mg), δ (d$_4$-MeOH) 1.33–1.75, m and 1.82, m, >10H, —(CH$_2$-)$_6$O(CH$_2$)$_3$—; 2.41, s, 3H, —SCH$_3$; 2.60, t, 2H, —CH$_2$Ph; 2.94–3.19, m, 4H, —CH$_2$NHCH$_2$—; 3.38, t×2, 4H, —CH$_2$OCH$_2$—; 4.80, m, —CHOH; 6.21, t, 1H and 6.37, d, 2H, resorcinol aromatic CH; 7.05–7.25, m, 6H, 7.38, td, 1H, 7.61, d, 1H, 7.78, d, 1H and 8.42, s, 1H, Ph and naphthalene aromatic CH.

Analysis Found: C, 64.77; H, 7.30; N, 2.34. C$_{23}$H$_{35}$NO$_4$S.C$_{11}$H$_8$O$_3$.1.05H$_2$O requires C, 64.95; H, 7.23; N, 2.23% Water Analysis 3.01% w/w.

The following are examples of suitable formulations of compounds of the invention. The term "active ingredient" is used herein to represent a compound of the invention.

Tablets

These may be prepared by the normal methods as wet granulation or direct compression.

A. Direct Compression

|  | mg/tablet |
|---|---|
| Active Ingredient | 2.0 |
| Microcrystalline Cellulose USP | 196.5 |
| Magnesium Stearate BP | 1.5 |
| Compression weight | 200.0 |

The active ingredient is seived through a suitable sieve, blended with the excipients and compressed using 7 mm diameter punches.

Tablets of other strengths may be prepared by altering the ratio of active ingredient to microcrystalline cellulose or the compression weight and using punches to suit.

B. For buccal administration

|  | mg/tablet |
|---|---|
| Active Ingredient | 2.0 |
| Lactose BP | 94.8 |
| Sucrose BP | 86.7 |
| Hydroxypropylmethylcellulose | 15.0 |
| Magnesium Stearate BP | 1.5 |
| Compression weight | 200.0 |

The active ingredient is sieved through a suitable sieve and blended with the lactose, sucrose and hydroxypropylmethylcellulose. Suitable volumes of purified water are added and the powders are granulated. After drying, the granules are screened and blended with the magnesium stearate. The granules are then compressed into tablets using suitable punches.

The tablets may be film coated with suitable film forming materials, such as hydroxypropyl methylcellulose, using standard techniques. Alternatively the tablets may be sugar coated.

Capsules

|  | mg/capsule |
|---|---|
| Active ingredient | 2.0 |
| *Starch 1500 | 97.0 |
| Magnesium Stearate BP | 1.0 |

-continued

|  | mg/capsule |
|---|---|
| Fill weight | 100.0 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

Syrup

This may be either a sucrose or sucrose free presentation.

A. Sucrose Syrup

|  | mg/5 ml dose |
|---|---|
| Active Ingredient | 2.0 |
| Sucrose BP | 2750.0 |
| Glycerine BP | 500.0 |
| Buffer | |
| Flavour | |
| Colour | as required |
| Preservative | |
| Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup produced is clarified by filtration.

B. Sucrose-Free

|  | mg/5 ml dose |
|---|---|
| Active ingredient | 2.0 mg |
| Hydroxypropyl methylcellulose USP (viscosity type 4000) | 22.5 mg |
| Buffer | |
| Flavour | |
| Colour | as required |
| Preservative | |
| Sweetener | |
| Purified Water BP to | 5.0 ml |

The hydroxypropyl methylcellulose is dispersed in hot water, cooled and then mixed with an aqueous solution containing the active ingredient and the other components of the formulation. The resultant solution is adjusted to volume and mixed. The syrup is clarified by filtration.

Metered Dose Presurised Aerosol

|  | mg/metered dose | Per can |
|---|---|---|
| A. Suspension Aerosol | | |
| Active ingredient micronised | 0.100 | 26.40 mg |
| Oleic Acid BP | 0.100 | 2.64 mg |
| Trichloroflouromethane BP | 23.64 | 5.67 g |
| Dichlorodifluoromethane BP | 61.25 | 14.70 |

The active ingredient is micronised in a fluid energy mill to a fine particle size range. The Oleic Acid is mixed with the Trichlorofluoromethane at a temperature of 10°–15° C. and the micronised drug is mixed into the solution with a high shear mixer. The suspension is metered into aluminium aerosol cans and suitable meterinf valves, delivering 85 mg of suspension are crimped onto the cans and the Dichlorodifluoromethane is pressure filled into the cans through the valves.

B. Solution Aerosol

|  | mg/metered dose | Per can |
|---|---|---|
| Active ingredient | 0.055 | 13.20 mg |
| Ethanol BP | 11.100 | 2.66 g |
| Dichlorotetrafluoroethane BP | 25.160 | 6.04 g |
| Dichlorodifluoromethane BP | 37.740 | 9.06 g |

Oleic acid BP, or a suitable surfactant e.g. Span 85 (sorbitan trioleate) may also be included.

The active ingredient is dissolved in the ethanol together with the oleic acid or surfactant if used. The alcoholic solution is metered into suitable aerosol containers followed by the dichlorotetrafluoroethane. Suitable metering valves are crimped onto the containers and dichlorodifluoromethane is pressure filled into them through the valves.

Suppositories

| Active ingredient | 2.0 mg |
|---|---|
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

Injection for Intravenous Administration

|  | mg/ml |
|---|---|
| Active ingredient | 0.5 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

Inhalation Cartridges

|  | mg/cartridge |
|---|---|
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

We claim:

1. A compound of formula (I)

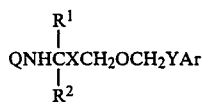

wherein

Ar represents a phenyl group optionally substituted by one or more substituents selected from halogen atoms, or the groups $C_{1-6}$alkyl, $C_{1-6}$alkoxy, nitro, —$(CH_2)_qR$ [where R is hydroxy, —$NR^3R^4$ (where $R^3$ and $R^4$ each represent a hydrogen atom or a $C_{1-4}$ alkyl group, or —$NR^3R^4$ forms a saturated heterocyclic amino group which has 5–7 ring members and optionally contains in the ring one or more atoms selected from —O— or —S— or a group —NH— or —N(CH$_3$)—), —$NR^5COR^6$ (where $R^5$ represents a hydrogen atom or a $C_{1-4}$ alkyl group, and $R^6$ represents a hydrogen atom or a $C_{1-4}$ alkyl, $C_{1-4}$ alkoxy, phenyl or —$NR^3R^4$ group), —$NR^5SO_2R^7$ (where $R^7$ represents a $C_{1-4}$alkyl, phenyl or —$NR^3R^4$ group), —$COR^8$ (where $R^8$ represents hydroxy, $C_{1-4}$ alkoxy or —$NR^3R^4$), —$SR^9$ (where $R^9$ is a hydrogen atom, or a $C_{1-4}$ alkyl or phenyl group), —$SOR^9$, $SO_2R^9$, or —CN, and q represents an integer from 0 to 3], —$(CH_2)_rR^{10}$ (where $R^{10}$ is a $C_{1-4}$ alkoxy group and r represents an integer from 1 to 3) or —$O(CH_2)_tR^{11}$ (where $R^{11}$ represents a hydroxy or $C_{1-4}$ alkoxy group and t is an integer 2 or 3), or Ar is a phenyl ring substituted by an alkylenedioxy group of formula —$O(CH_2)_pO$— where p represents an integer 1 or 2;

Q represents a group of formula

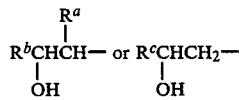

where $R^a$ represents a hydrogen atom or a $C_{1-3}$ alkyl group, $R^b$ represents

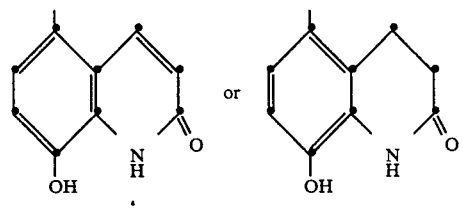

and Rc represents

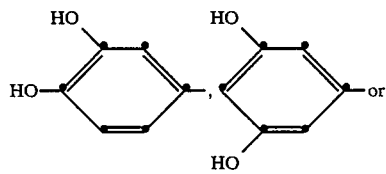

-continued

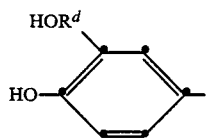

where $R^d$ represents a straight or branched $C_{2-3}$ alkylene chain;

$R^1$ and $R^2$ each represent a hydrogen atom or a $C_{1-3}$ alkyl group with the proviso that the sum total of carbon atoms in $R^1$ and $R^2$ is not more than 4;

X represents a $C_{1-7}$ alkylene, $C_{2-7}$ alkenylene or $C_{2-7}$ alkynylene chain; and Y represents a bond or a $C_{1-6}$ alkylene, $C_{2-6}$ alkenylene or $C_{2-6}$ alkynylene chain with the proviso that the sum total of carbon atoms in X and Y is 2–10, and physiologically acceptable salts and solvates thereof.

2. A compound according to claim 1 in which the total number of carbon atoms in the chains X and Y is 4 to 10 inclusive.

3. A compound according to claim 1, which the chain X is —(CH$_2$)$_2$—, —(CH$_2$)$_3$—, —(CH$_2$)$_4$—, —(CH$_2$)$_5$—, —(CH$_2$)$_6$—, —CH$_2$C≡C—, —(CH$_2$)$_2$CH═CH—, —(CH$_2$)$_2$C≡C—, —CH═CHCH$_2$—, —CH═CH(CH$_2$)$_2$— or —CH$_2$C≡CCH$_2$—, and the chain Y is —CH$_2$—, —(CH$_2$)$_2$—, —(CH$_2$)$_3$—, —(CH$_2$)$_4$—, —(CH$_2$)$_5$—, —(CH$_2$)$_6$—, —CH═CH—, —C≡C—, —CH$_2$CH═CH— or —CH$_2$C≡C—.

4. A compound according to claim 1, in which $R^1$ and $R^2$ are each methyl, ethyl, propyl or isopropyl groups except that if one of $R^1$ and $R^2$ is a propyl or isopropyl group, then the other is a hydrogen atom or a methyl group.

5. A compound according to claim 1, in which Ar represents an unsubstituted phenyl group or a phenyl group substituted by chlorine, bromine, iodine, fluorine, methyl, ethyl, methoxy, ethoxy, —(CH$_2$)$_q$R [where R is hydroxy, amino, methylamino, ethylamino, dimethylamino, diethylamino, morpholino, piperidine, pyrrolidino, piperazino, N-methylpiperazino, NHCOR$^6$ (where R$^6$ is hydrogen, C$_{1-4}$ alkyl, C$_{1-4}$ alkoxy, phenyl, amino or N,N-dimethylamino), —N(CH$_3$)COCH$_3$, —NR$^5$SO$_2$R$^7$ (where R$^5$ represents a hydrogen atom or a methyl group, and R$^7$ represents phenyl, methyl, butyl, amino or dimethylamino), —COOH, —COOCH$_3$, —COOCH$_2$CH$_2$CH$_3$, —CONH$_2$—, —CON(CH$_3$)$_2$, —CON(CH$_2$CH$_3$)$_2$, —CON(CH$_2$CH$_2$CH$_3$)$_2$,

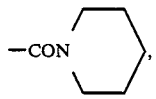

—SR$^9$ (where R$^9$ is methyl, ethyl or phenyl), —SOCH$_3$, —SO$_2$CH$_3$, or CN and q is zero, 1, 2 or 3], —NO$_2$, —CH$_2$OCH$_3$, —(CH$_2$)$_3$OCH$_3$, —O(CH$_2$)$_2$OH, —O(CH$_2$)$_3$OH, —O(CH$_2$)$_2$OCH$_3$, or —(CH$_2$)$_2$OCH$_2$CH$_3$.

6. A compound according to claim 1, in which Q represents

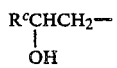

where $R^c$ represents

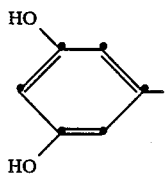

7. A compound according to claim 1, in which in the definition of Q, the group $R^a$ is a hydrogen atom or a methyl, ethyl, propyl or isopropyl group.

8. A compound according to claim 1, in which in the definition of Q, the chain $R^d$, if present, is —(CH$_2$)$_2$, —(CH$_2$)$_3$— or

9. A compound according to claim 1 which is: 2-Hydroxy-5-[1-hydroxy-2-[[6-[2-(4-methoxyphenyl)ethoxy]-hexyl]amino]ethyl]benzeneethanol;
2-Hydroxy-5-[1-hydroxy-2-[[1-methyl-6-(2-phenylethoxy)-hexyl]amino]ethyl]benzeneethanol;
5-[1-Hydroxy-2-[[1-methyl-6-(2-phenylethoxy)hexyl]amino]ethyl]-1,3-benzenediol;
5-[1-Hydroxy-2-[[6-(4-phenylbutoxy)hexyl]amino]ethyl]-1,3-benzenediol;
5-[1-hydroxy-2-[[1-methyl-5-[3-[4-(1-pyrrolidinyl)phenyl]propoxy]pentyl]amino]ethyl]-1,3-benzenediol;
5-[1-hydroxy-2-[[6-[3-[4-(methylthio)phenyl]propoxy]hexyl]amino]ethyl]-1,3-benzenediol;
4-[4-[[6-[[2-(3,5-dihydroxyphenyl)-2-hydroxyethyl]amino]hexyl]oxy]butyl]-N,N-diethylbenzamide;
5-[1-hydroxy-2-[[6-[2-[4-(1-pyrrolidinyl)phenyl]ethoxy]hexyl]amino]ethyl]-1,3-benzenediol; or a physiologically acceptable salt or solvate thereof.

10. A pharmaceutical composition comprising at least one compound of general formula (I) as defined in claim 1 or a physiologically acceptable salt or solvate thereof, together with a physiologically acceptable carrier or excipient.

* * * * *